US006143289A

United States Patent [19]
Broxmeyer et al.

[11] Patent Number: 6,143,289
[45] Date of Patent: Nov. 7, 2000

[54] COMPOSITIONS OF MYELOID-CELL-SUPPRESSIVE CHEMOKINES

[75] Inventors: Hal E. Broxmeyer; Scott Cooper; Charles Mantel; Li Lu, all of Indianapolis, Ind.

[73] Assignee: Indiana University Foundation, Bloomington, Ind.

[21] Appl. No.: 07/987,638

[22] Filed: Dec. 9, 1992

[51] Int. Cl.[7] .............................. A61K 38/19; C07K 14/52
[52] U.S. Cl. ............................ 424/85.2; 424/85.1; 514/2; 530/300
[58] Field of Search ............................... 435/240.1, 240.2; 514/2; 424/85.2, 85.1; 530/300

[56] References Cited

U.S. PATENT DOCUMENTS

| | | | |
|---|---|---|---|
| 5,185,323 | 2/1993 | Gewirtz | 514/12 |
| 5,294,544 | 3/1994 | Gentile et al. | 435/70.4 |
| 5,306,709 | 4/1994 | Gewirtz | 514/12 |

OTHER PUBLICATIONS

Bennett et al BBRC vol. 101 pp. 88–95, 1981.
Broxmeyer, et al., "The Production of Myeloid Blood Cells and Their Regulation During Health and Disease", *CRC Crit. Rev. Oncol/Hematol.*, vol. 8, pp. 173–226 (1988).
Broxmeyer, "Biomolecule–cell Interactions and the Regulation of Myelopoiesis, An Update", in Murphy Jr. (ed): *Concise Reviews in Clinical and Experimental Hematology,* Dayton, Ohio, Alpha Med Press, pp. 119–148 (1992).
Broxmeyer, "Suppressor Cytokines and Regulation on Myelopoiesis: Biology and Possible Clinical Uses",*Amer. J. Ped. Hematol/Oncol.*, vol. 14, pp. 22–30 (1992).
Wolpe, et al., "Macrophages Secrete A Novel Heparin–Binding Protein with inflammatory and Neutrophil Chemokinetic Properties", *J. Exp. Med.*, vol. 167, pp. 570–581 (1980).
Davatelis, et al., "Cloning and Characerization of a cDNA for Murine Macrophage Inflammatory Protein (MIP), a Novel Monokine with Inflammatory and Chemokinetic Properties", *J. Exp. Med.*, vol. 167, pp. 1939–1944 (1988).
Graham et al., "Identification and Characterization of an Inhibitor of Hematopoietic Stem Cell Proliferation", *Nature,* vol. 334, pp. 442–444 (1990).
Broxmeyer, et al., "Enhancing and Suppressing Effects of Recombinant Murine Macrophage Inflammatory Proteins on Colony Formation in vitro by Bone Marrow Myeloid Progenitor Cells", *Blood,* vol. 76, p. 1110 (1990).
Bodine, et al., "Effects of Hematopoietic Growth Factors on the Survival of Primitive Stem Cells in Liquid Suspension Culture", *Blood,* vol. 78, pp. 914–920 (1991).
Broxmeyer, et al., "Macrophage Inflammatory Protein (MIP)–1β Abrogates the Capacity of MIP–1α to Suppress Myeloid Progenitor Cell Growth", *J. Immunol.*, vol. 147,pp. 2586–2594 (1991).
Maze, et al., "Myelosuppressive Effects in vivo of Purified Recombinant Murine Macrophage Inflammatory Protein–1 Alpha", *J. Immunol.*, vol. 149, pp. 1004–1009 (1992).

(List continued on next page.)

*Primary Examiner*—Ponnathapu Achutamurthy
*Assistant Examiner*—William Moore
*Attorney, Agent, or Firm*—Woodard, Emhardt, Naughton, Moriarty & McNett

[57] ABSTRACT

Described are preferred processes for suppressing proliferation of or for myeloprotecting myeloid cells in mammals. The processes involve the use of chemokines of the group Macrophage Inflammatory Protein-2α (MIP-2α), Platelet Factor 4 (PF4), Interleukin-8 (IL-8) and Macrophage Chemotactic and Activating Factor (MCAF), or involve the use of these chemokines or Macrophage Inflammatory Protein-1α (MIP-1α) in synergistic combinations or while they are substantially completely in monomeric form (i.e. substantially free from their polymerized or aggregated forms).

22 Claims, 11 Drawing Sheets

OTHER PUBLICATIONS

Dunlop, et al., "Demonstration of Stem Cell Inhibition and Myeloprotective Effects of SCI/rhMIP–1α in vivo", *Blood*, vol. 79, pp. 2221–2225 (1992).

Lord, et al., "Macrophage–Inflammatory Protein Protects Multipotent Hamatopoietic Cells from the Cytotoxic Effects of Hydroxyurea in vivo", *Blood*, vol. 79, pp. 2605–2609 (1992).

Oh, et al., Identification of Cell Surface Receptors for Murine Macrophage Inflammatory Protein–1α, *J. Immunol.*, vol. 147, p. 2978 (1991).

Fahey, et al., "Macrophage Inflammatory Protein 1 Modulates Macrophage Function", *J. Immunol.*, vol. 148, pp. 2764–2769 (1992).

Wolpe, et al., "Macrophage Inflammatory Proteins 1 and 2: Members of a Novel Superfamily of Cytokines", *FASEB J.*, vol. 3, p. 2565–2573 (1989).

Oppenheim, et al., "Properties of the Novel Proinflammatory Supergene 'Intercrine' Cytokine Family", *Ann. Ref. Immunol.*, vol. 9, p. 617 (1991).

Schall, "Biology of the Rants/Sis Cytokine Family", *Cytokine*, vol. 3, p. 165 (1991).

Lu, et al., "Characterization of Adult Human Marrow Hematopoietic Progenitors Highly Enriched by Two–Color Sorting with My10 and Major Histocompatibility (MHC) Class II Monoclonal Histocompatibility (MHC) Class II Monoclonal Antibodies", *J. Immunol.*, vol. 139, pp. 1823–1829 (1987).

Tekamp–Olson et al., "Cloning and Characerization of cDNAs for Murine Macrophage Inflammatory Proein 2 and Its Human Homologues", *J. Exp. Med.*, vol. 172, pp. 911–919 (1991).

Broxmeyer, et al., "Effect of Murine Mast Cell Growth Factor (c–kit Proto–oncogene Ligand) on Colony Formation by Human Marow Hematopoietic Progenitor Cells", *Blood*, vol. 77, pp. 2142 (1991).

Gewirta et al., "Inhibition Of Human Megakaryocytopoiesis in Vitro by Platelet Factor 4 (PF4) and a Synthetic COOH–Terminal PF4 Peptide", *J. Clin. Invest.*, vol. 83, pp. 1477–1486 (1989).

COMPOSITIONS OF MYELOID-CELL-SUPPRESSIVE CHEMOKINES

BACKGROUND

The present invention resides generally in the field of regulation of myeloid cells such as stem cells or progenitor cells. More particularly, the present invention relates to the suppression of the proliferation of or the myeloprotection of mammalian myeloid cells using selected chemokines.

As further background, accessory cell-derived cytokines regulate proliferation/differentiation of hematopoietic stem and progenitor cells in vitro and in vivo. See, Broxmeyer, et al., "The Production of Myeloid Blood Cells and Their Regulation During Health and Disease", CRC Crit, Rev. Oncol/Hematol., Vol. 8, p. 173 (1988); and Broxmeyer, "Biomolecule-cell Interactions and the Regulation of Myelopoiesis, An Update", in Murphy Jr. (ed): Concise Reviews in Clinical and Experimental Hematology, Dayton, Ohio, Alpha Med Press, p. 119 (1992). Cytokines can have stimulating, enhancing, and/or suppressing activities mediated either directly on stem/progenitor cells and/or indirectly on accessory cells.

A number of cytokines have been implicated in negative regulation. See, Broxmeyer, et al., "The Production of Myeloid Blood Cells and Their Regulation During Health and Disease", supra; Broxmeyer, "Biomolecule-cell Interactions and the Regulation of Myelopoiesis, An Update", supra; and Broxmeyer, "Suppressor Cytokines and Regulation on Myelopoiesis: Biology and Possible Clinical Uses", Amer. J. Ped. Hematol/Oncol, Vol. 14, p. 22 (1992). Suppression can be mediated by biological molecules termed cytokines, such as macrophage inflammatory protein (MIP)-1α, a heparin binding protein originally identified by its capacity to cause a localized inflammatory reaction after injection into the footpads of C3H/HeJ mice. See, Wolpe, et al., "Macrophages Secrete A Novel Heparin-Binding Protein with Inflammatory and Neutrophil Chemokinetic Properties", J. Exp. Med., Vol. 167, p. 570 (1980); Davatelis, et al., "Cloning and Characterization of a CDNA for Murine Macrophage Inflammatory Protein (MIP), a Novel Monokine with Inflammatory and Chemokinetic Properties", J. Exp. Med., Vol. 167, p. 1939 (1988); and Sherry, et al., "Resolution of the Two Components of Macrophage Inflammatory Protein 1, and Cloning and Characterization of One of Those Components, Macrophage Inflammatory Protein 1B", J. Exp. Med., Vol. 168, p. 2251 (1988).

MIP-1α, but not a closely related family member MIP-1β, suppressed proliferation of a subset of murine (mu) stem cells (day 12 colony forming-unit-spleen (CFU-S)) ex vivo and mu colony forming unit-A (an apparently early progenitor cell) (see, Graham et al., "Identification and Characterization of an Inhibitor of Hematopoietic Stem Cell Proliferation", Nature, Vol. 334, p. 442 (1990)), as well as mu and human (hu) growth-factor stimulated multipotential (CFU-GEMM), erythroid (BFU-E) and granulocyte macrophage (CFU-GM) progenitor cells (see, Broxmeyer, et al., "Enhancing and Suppressing Effects of Recombinant Murine Macrophage Inflammatory Proteins on Colony Formation in vitro by Bone Marrow Myeloid Progenitor Cells", Blood, Vol. 76, p. 1110 (1990)) in vitro. Suppressive effects of MIP-1α were apparent on more immature populations of progenitors which were stimulated to proliferate by a combination of two or more early acting growth stimulating cytokines. See, Broxmeyer, et al., "Enhancing and Suppressing Effects of Recombinant Murine Macrophage Inflammatory Proteins on Colony Formation in vitro by Bone Marrow Myeloid Progenitor Cells", Blood, Vol. 76, p. 1110 (1990); and Bodine, et al., "Effects of Hematopoietic Growth Factors on the Survival of Primitive Stem Cells in Liquid Suspension Culture", Blood, Vol. 78, p. 914 (1991). These effects appeared to be directly on the progenitors themselves. See, Broxmeyer, et al., "Macrophage Inflammatory Protein (MIP)-1β Abrogates the Capacity of MIP-1α to Suppress Myeloid Progenitor Cell Growth", J. Immunol., Vol. 147, p. 2586 (1991). MIP-1α did not suppress proliferation of the more mature progenitors which were stimulated to proliferate by a single cytokine. See, Broxmeyer, et al., "Enhancing and Suppressing Effects of Recombinant Murine Macrophage Inflammatory Proteins on Colony Formation in vitro by Bone Marrow Myeloid Progenitor Cells", supra; and Broxmeyer, et al., "Macrophage Inflammatory Protein (MIP)-1β Abrogates the Capacity of MIP-1α to Suppress Myeloid Progenitor Cell Growth", supra.

MIP-1α has recently been shown to have in vivo suppressive effects on cycling rates of CFU-S, CFU-GEMM, BFU-E an CFU-GM when administered to mice (see, Maze, et al., "Myelosuppressive Effects in vivo of Purified Recombinant Murine Macrophage Inflammatory Protein-1 Alpha", J. Immunol., Vol. 149, p. 1004 (1992); Dunlop, et al., "Demonstration of Stem Cell Inhibition and Myeloprotective Effects of SCI/rhMIP-1α in vivo", Blood, Vol. 79, p. 2221 (1992); and Lord, et al., "Macrophage-Inflammatory Protein Protects Multipotent Hamatopoietic Cells from the Cytotoxic Effects of Hydroxyurea in vivo", Blood, Vol. 79, p. 2605 (1992)), and in this context was myeloprotective for the drugs cytosine arabinoside (see, Dunlop, et al., supra) and hydroxyurea (see, Lord, et al., supra.) MIP-1β was not myelosuppressive in vivo. See, Maze, et al., supra.

MIP-1α also inhibited proliferation of an unstimulated cytotoxic T-cell line, CTLL-R8 (see, Oh, et al., Identification of Cell Surface Receptors for Murine Macrophage Inflammatory Protein-1α", J. Immunol., Vol. 147, p. 2978 (1991)), and modulated macrophage function, including induction of the release of tumor necrosis-factor, interleukin (IL)-1α and IL-6 in vitro. See, Fahey, et al., "Macrophage Inflammatory Protein 1 Modulates Macrophage Function", J. Immunol., Vol. 148, p. 2764 (1992). MIP-1β, when present in excess compared to MIP-1α in vitro, blocked both the suppressive effects of MIP-1α on myeloid progenitors (see, Broxmeyer, et al., "Macrophage Inflammatory Protein (MIP)-1β Abrogates the Capacity of MIP-1α to Suppress Myeloid Progenitor Cell Growth", supra), and the cytokine-inducing effects of MIP-1α on macrophages. See, Fahey, et al., supra.

MIP-1α and MIP-1β are members of a larger family of molecules variously termed small inducible proteins, intercrine cytokines (see, Wolpe, et al., "Macrophage Inflammatory Proteins 1 and 2: Members of a Novel Superfamily of Cytokines", FASEB, J., Vol. 3, p. 2565 (1989); Oppenheim, et al., "Properties of the Novel Proinflammatory Supergene 'Intercrine' Cytokine Family", Ann. Ref. Immunol., Vol. 9, p. 617 (1991); and Schall, "Biology of the Rantes/Sis Cytokine Family", Cytokine, Vol. 3, pp 165 (1991)), and more recently, chemokines. They are linked by amino acid homology, chromosome location and the presence in their primary sequence of 4 position invariant cysteine residues. The hu MIP-1 family, located on chromosome 17 and having a c—c motif, includes MIP-1α (=LD78), MIP-1β (=Act 2), Macrophage Chemotactic and Activating Factor (MCAF= muJE) and RANTES. The hu MIP-2 family located on chromosome 4 and having a c-x-c motif, includes GRO-α (also called melanoma growth stimulating factor=muKC), MIP-2α (=GRO-β), MIP-2β (=GRO-γ), Platelet Factor 4 (PF4), IL-8 (=neutrophil activating peptide (NAP)-1) and NAP-2 (which derives from platelet basic protein an its derivatives connective tissue activating peptide III and β-thromboglobulin).

SUMMARY OF THE INVENTION

One preferred embodiment of the present invention provides a process for suppressing proliferation of or for myeloprotecting myeloid cells in a mammal. The process comprises administering to a mammal for which such suppression or myeloprotection is desired an effective amount of at least one chemokine selected from the group consisting of Macrophage Inflammatory Protein-2α (MIP-2α), Platelet Factor 4 (PF4), Interleukin-8 (IL-8) and Macrophage Chemotactic and Activating Factor (MCAF).

Another preferred embodiment of the present invention provides a process for suppressing proliferation of or for myeloprotecting myeloid cells in a mammal. The process comprises administering to a mammal for which such suppression or myeloprotection is desired a synergistic combination of chemokines selected from the group consisting of MIP-1α, MIP-2α, PF4, IL-8 and MCAF.

Another preferred embodiment of the present invention provides a process for suppressing proliferation of or for myeloprotecting myeloid cells in a mammal. The process comprises administering to a mammal for which such suppression or myeloprotection is desired at least one chemokine substantially in monomeric form and selected from the group consisting of MIP-1α, MIP-2α, PF4, IL-8 and MCAF.

Another preferred embodiment of the present invention provides a process for suppressing proliferation of or for myeloprotecting myeloid cells in a mammalian bone marrow cell population stimulated by multiple growth stimulating cytokines (such as a combination of colony stimulating factors, or one or more colony stimulating factors with another cytokine such as Steel Factor, c-kit ligand) in a culture medium. The process comprises including in said cell population a synergistic combination of at least two chemokines selected from the group consisting of MIP-1α, MIP-2α, PF4, IL-8 and MCAF.

Still another preferred embodiment of the invention provides a composition which comprises a mammalian bone marrow cell population stimulated by multiple growth stimulating cytokines in a culture medium and having suppressed proliferation of or myeloprotection of myeloid cells by a synergistic combination of at least two chemokines selected from the group consisting of MIP-1α, MIP-2α, PF4, IL-8 and MCAF.

Another preferred embodiment of the present invention provides a process for blocking the myelosuppressive activity of IL-8 or PF4, comprising blocking said myelosuppressive activity with an effective amount of a chemokine selected from the group consisting of MIP-2β and GRO-α.

Still another preferred embodiment of the invention provides a composition comprising a solution of one or more chemokines predominantly in monomeric form and selected from the group consisting of MIP-1α, MIP-2α, PF4, IL-8 and MCAF.

Advantageously, when using synergistic combinations of chemokines in methods of the invention, the chemokines are effective at concentrations far below those necessary when the chemokines are used individually. Likewise, when compositions containing the chemokines predominantly in monomeric form are used, far less of the chemokine material needs to be used to achieve advantageous suppression of myeloid cell proliferation.

Methods and compositions of the present invention thus provide myeloprotectant effects which can be used in conjunction with therapies which may adversely affect myeloid cells. For example, administration of chemokines according to the invention, e.g. by injection into the mammal to undergo therapy, can place myeloid cells in a myeloprotected, slow-cycling state. Cell damage caused by subsequent radiation therapy or chemotherapy using cell-cycle active drugs, such as cytosine arabinoside and hydroxyurea, can thereby be reduced.

Methods and compositions of the invention also provide myelosuppressive effects which can be used in the treatment of disorders such as leukemia that cause hyperproliferative myeloid cell states or of disorders causing hypoproliferative myeloid cell states. Administration of chemokines according to the invention, e.g. by injection intravenously or subcutaneously, can suppress proliferation of myeloid cells, or can block suppression of myeloid cells.

Methods and compositions of the invention also provide for suppressed, myeloprotected or suppression-blocked myeloid cell populations which can be used in ex vivo therapies or in studies of disorders such as leukemia or of side-effects such as those resulting from radiation- or chemo-therapy, e.g. in this regard in the screening of agents or therapies for their adverse or modulative effects on myeloid cells.

Additional embodiments, objects and advantages of the invention will be apparent from the description herein.

DESCRIPTION

Figure 1A:
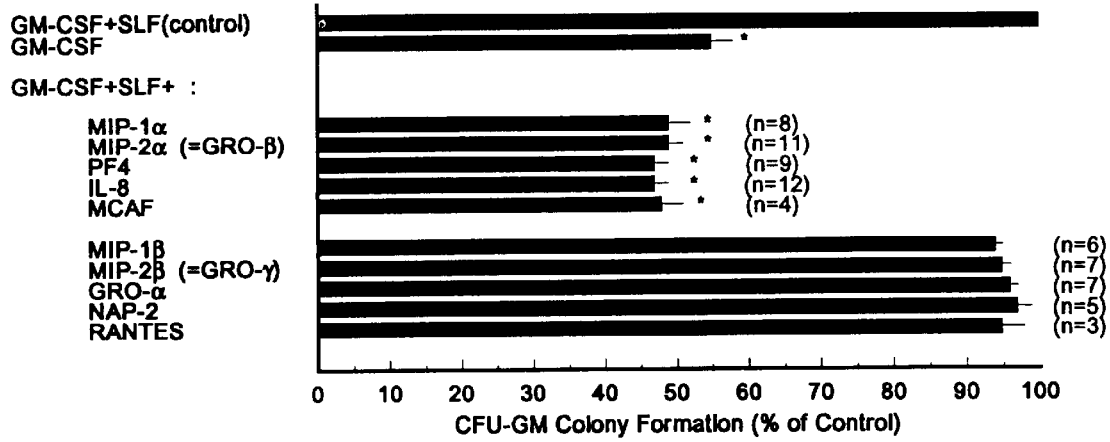
FIG. 1: Influence of chemokine molecules on colony formation by A) CFU-GM, B) BFU-E, and C) CFU-GEMM in $10^5$ low density normal human bone marrow cells. Control colony numbers for CFU-GM plated in the presence of GM-CSF plus SLF, and for BFU-E and CFU-GEMM plated in the presence of Epo plus SLF were respectively: 130±13 (mean±1 SEM, range: 59 to 197 for 13 marrows), 83±11 (range: 45 to 162 for 11 marrows), and 38±6 (range: 11 to 71 for 11 marrows). "*" designates significant change, p<0.01 compared to control values; other values were not significantly different from control, p>0.05. n in parenthesis designates the number of different test marrows studied.

For the purposes of promoting an understanding of the principles of the invention, reference will now be made to preferred embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention pertains.

The following abbreviations are used herein: MIP, macrophage inflammatory protein; MCAF, macrophage chemotactic and activating factor; PF4, platelet factor 4; IL, interleukin; NAP, neutrophil activating peptide; CFU-GEMM, multipotential progenitor cell; BFU-E, erythroid progenitor cell; CFU-GM, granulocyte macrophage progenitor cell; CSF, colony stimulating factor(s); GM, granulocyte macrophage; Epo, erythropoietin; NALDT⁻, non-adherent low density T-lymphocyte depleted; mu, murine; hu, human; r, recombinant; CFU-S, colony forming unit spleen, a subset of the pluripotent stem cells; LD, low density; SLF, steel factor.

Cells and Cell Separation Procedures

Hu bone marrow cells were obtained by aspiration from the posterior iliac crest of healthy volunteers who had given informed consent. Low density cells (LD,<1.077 g/cm$^3$) were retrieved after density cut separation on Ficoll-Hypaque (Pharmacia Fine Chemicals, Piscataway, N.J.). Hu bone marrow was further enriched for myeloid progenitor cells by obtaining fractions of non-adherent low density T-lymphocyte depleted (NADLT$^-$) fluorescence-activated cell-sorted CD34$^{+++}$ HLA-DR$^+$ cells. See, Lu, et al., "Characterization of Adult Human Marrow Hematopoietic Progenitors Highly Enriched by Two-Color Sorting with My10 and Major Histocompatibility (MHC) Class II Monoclonal Antibodies", *J. Immunol.*, Vol. 139, pp. 1823 (1987). A Coulter 753 Flow Cytometry System (Hialeah, Fla.) was used to sort for the highest density of CD34$^{+++}$ cells which represent approximately 1% of the starting population of NALDT$^-$ cells and is most enriched for progenitor cells within the total population of CD34 expressing cells. See, Broxmeyer, et al., "Enhancing and Suppressing Effects of Recombinant Murine Macrophage Inflammatory Proteins on Colony Formation in vitro by Bone Marrow Myeloid Progenitor Cells", supra.

Hu Cytokines

All cytokines were purified. Recombinant MIP-1α, MIP-1β, MIP-2α and MIP-2β were produced using yeast expression vectors (see, Tekamp-Olson et al., "Cloning and Characterization of cDNAs for Murine Macrophage Inflammatory Protein 2 and Its Human Homologues", *J. Exp. Med.*, Vol. 172, pp. 911 (1990)) and were obtained from Chiron Corp. Emeryville, Calif. Recombinant GRO-α was from Immunex Corp., Seattle, Wash. Recombinant preparations of MCAF, RANTES and the 77 and 72 amino acid forms of IL-8 were purchased from Pepro Tech, Inc., Rocky Hills, N.J. The 77 amino acid form of recombinant IL-8 and the natural form of PF4 were purchased from Sigma Chemical Co., St. Louis, Mo. Recombinant NAP-2 was purchased from Bachem Bioscience, Philadelphia, Pa. Recombinant erythropoietin (Epo) was purchased from Amgen Corp., Thousand Oaks, Calif. Recombinant granulocyte-macrophage colony stimulating factor (GM-CSF), IL-3 and Steel Factor (SLF, also called mast cell growth factor, stem cell factor and c-kit ligand) were from Immunex Corp.

Colony Assays.

LD and NALDT$^-$ cells were respectfully plated at $10^5$ and $2.5 \times 10^4$ cells/ml in either 0.3% agar culture medium for assessment of CFU-GM or in 0.9% methylcellulose culture medium for assessment of CFU-GEMM and BFU-E as described previously in Broxmeyer, et al., "Enhancing and Suppressing Effects of Recombinant Murine Macrophage Inflammatory Proteins on Colony Formation in vitro by Bone Marrow Myeloid Progenitor Cells", supra; Broxmeyer, et al., "Macrophage Inflammatory Protein (MIP)-1β Abrogates the Capacity of MIP-1α to Suppress Myeloid Progenitor Cell Growth", supra; and Broxmeyer, et al., "Effect of Murine Mast Cell Growth Factor (c-kit Proto-oncogene Ligand) on Colony Formation by Human Marrow Hematopoietic Progenitor Cells", *Blood*, Vol. 77, pp. 2142 (1991). CFU-GM colonies (>40 cells/group) were stimulated by rhuGM-CSF (100 U/ml), alone or in combination with rhuSLF (50 ng/ml) and CFU-GEMM and BFU-E colonies were stimulated by rhuEpo (1–2 U/ml), alone or in combination with rhuSLF (50 ng/ml). NALDT$^-$ CD34$^{+++}$ HLA-DR$^+$ cells were plated in methylcellulose with Epo (2 U/ml), SLF (50 ng/ml), IL-3 (200 U/ml) and GM-CSF (200 U/ml) at concentrations ranging from 100 to 400 cells/ml. The concentrations of GM-CSF and Epo used give plateau numbers of colonies when used alone, and SLF syntergises with either Epo or GM-CSF to respectfully enhance the numbers and size of CFU-GEMM/BFU-E and CFU-GM colonies. See, Broxmeyer, et al., "Effect of Murine Mast Cell Growth Factor (c-kit Proto-oncogene Ligand) on Colony Formation by Human Marrow Hematopoietic Progenitor Cells", supra. Colonies were scored after 14 days incubation at lowered (5%) $O_2$ tension, and 5% $CO_2$ in a humidified environment in an ESPEC $N_2$—$O_2$—$CO_2$ incubator BNP-210 (Taboi ESPEC Corp., South Plainfield, N.J.). Three plates were scored per determination.

Statistics

Levels of significance were determined using student's t distribution (2 tailed test).

Results

Influence of Chemokines on Colony Formation rhu preparations of MIP-1α, MIP-1β, MIP-2α, MIP-2β, IL-8, MCAF, GRO-α, NAP-2, RANTES, and natural hu PF4 were each assessed at concentrations of 10, 25, 50, 100 and 1000 ng/ml for effects on colony formation by $10^5$ low density bone marrow cells/ml. Cells were plated either in the absence of added colony stimulating factors, or in the presence of rhuGM-CSF (100 U/ml) -/+ rhuSLF (50 ng/ml) for CFU-GM, and rhuEpo (1 U/ml) -/+rhuSLF (50 ng/ml) for CFU-GEMM and BFU-E. In the absence of added colony stimulating factors, no CFU-GM, BFU-E or CFU-GEMM colonies grew, and none of the chemokines at the concentrations tested stimulated colony formation. Moreover, the chemokines had no significant effect on colony formation of CFU-GM stimulated by maximally effective concentrations of GM-CSF or of BFU-E and CFU-GEMM stimulated by maximal levels of Epo. (For example, the percentage change from control values for each assay in the presence of chemokines ranged from–8 to +10, p>0.05, based on respective control colony numbers of CFU-GM, BFU-E and CFU-GEMM of 25 to 55, 15 to 35 and 1 to 3).

Figure 1B:
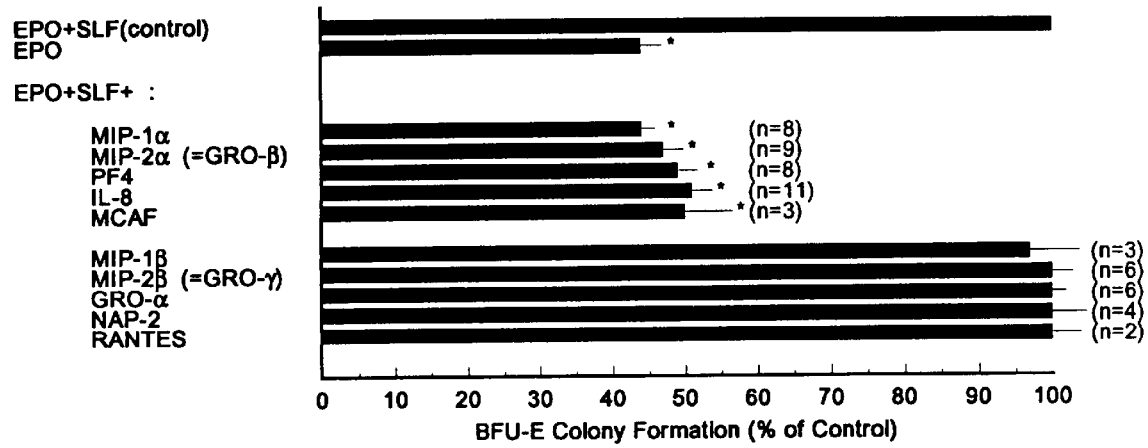
Figure 1C:
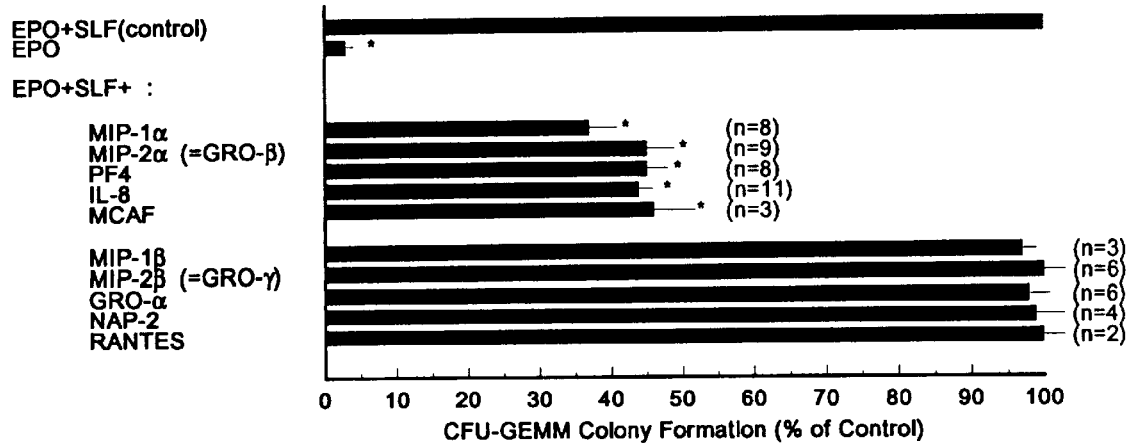

Chemokines were also each assessed at 100 ng for effects on CFU-GM colony formation stimulated by the combination of GM-CSF and SLF (FIG. 1A), and on BFU-E (FIG. 1B) and CFU-GEMM (FIG. 1C) colony formation stimulated by Epo and SLF. MIP-1α, MIP-2α, PF4, IL-8 and MCAF each significantly reduced total colony formation of CFU-GM, BFU-E and CFU-GEMM by about 50% (p<0.01) and completely suppressed the SLF-enhanced colony formation of CFU-GM and BFU-E. The different forms of IL-8, which included the 72 amino acid samples from two different companies or the 77 amino acid sample, were equally suppressive. Maximum suppression was apparent with 100 ng/ml of each cytokine. No greater suppression was noted when concentrations up to 1000 ng/ml were used. The suppressive effects were lost between 25–50 ng/ml. MIP-1β, MIP-2β, GRO-α, NAP-2 and RANTES did not influence colony formation by myeloid progenitors at 100 ng/ml (FIG. 1A, B, C) or at 1000 ng/ml. Thus, the hu preparations of MIP-1α, MIP-2α, MIP-2α, PF4, IL-8 and MCAF have myelosuppressive effects similar to rmuMIP-α, (see, Broxmeyer, et al., "Enhancing and Suppressing Effects of Recombinant Murine Macrophage Inflammatory Proteins on Colony Formation in vitro by Bone Marrow Myeloid Progenitor Cells", supra; and Broxmeyer, et al., "Macrophage Inflammatory Protein (MIP)-1β Abrogates the Capacity of MIP-1α to Suppress Myeloid Progenitor Cell Growth", *J. Immunol.*, Vol. 147, pp. 2586 (1991))

Effects on Purified Myeloid Progenitor Cells

Figure 2:
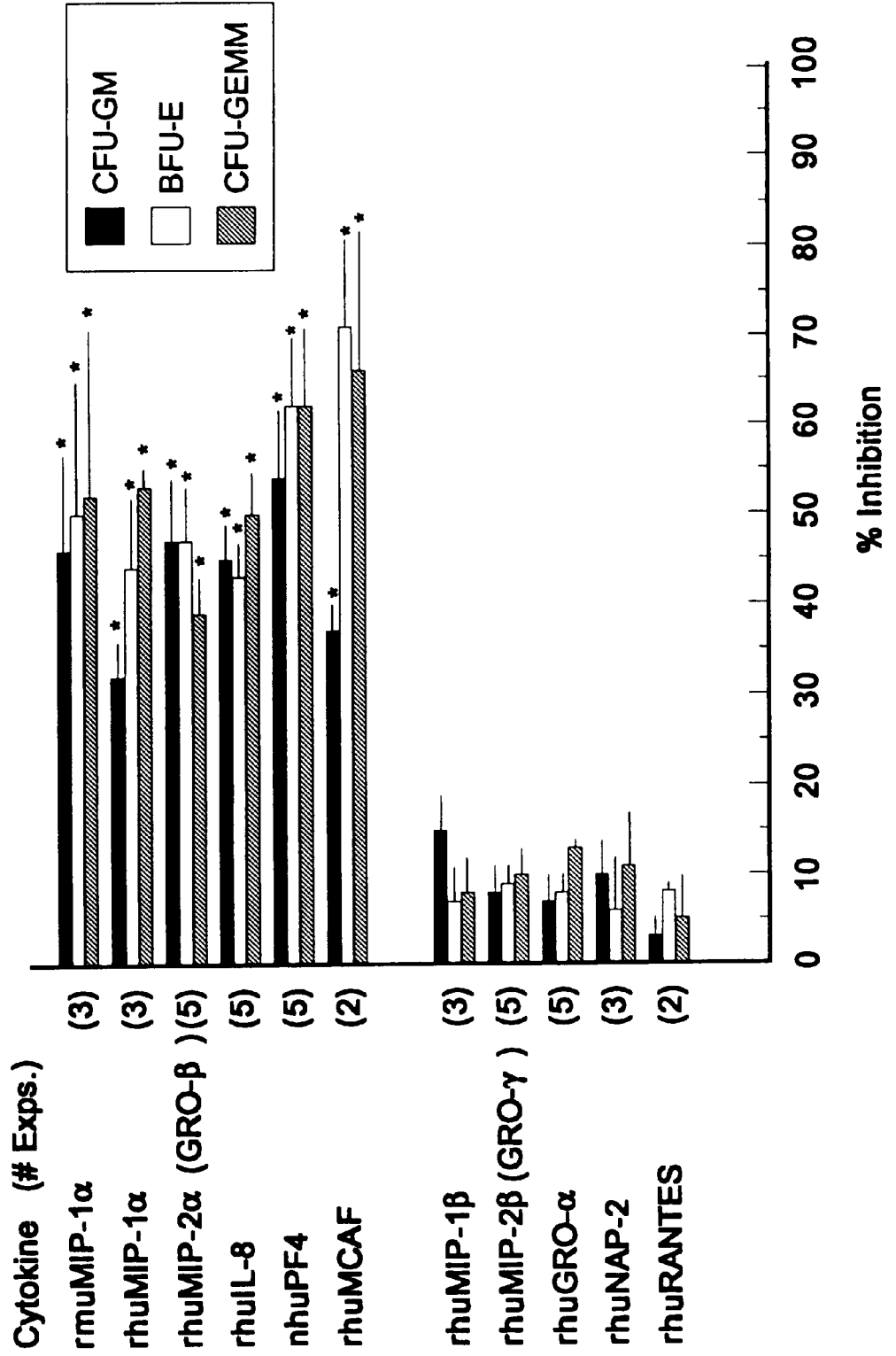
FIG. 2: Percent inhibition of colony formation by highly enriched populations of myeloid progenitor cells present in NALDT$^-$ CD34$^{+++}$ HLA-DR$^+$ normal human bone marrow cells. Cloning efficiencies scored from the same plates for 100 to 400 cells plated/ml for CFU-GM plus BFU-E plus CFU-GEMM averaged 53±7% (mean =/−1 SEM; range: 32 to 77% for 5 experiments). "*" designates p<0.01 compared to growth without chemokines molecules; other values not significantly different, p>0.05.

To evidence whether the effects of the chemokines on colony formation by human bone marrow cells are direct acting on the progenitor cells, each hu chemokine was assessed at 100 ng/ml for effects on colony formation by 100 to 400 NALDT⁻ CD34⁺⁺⁺ HLA-DR⁺ cell/ml stimulated by the combination of Epo (2 U/ml), SLF (50 ng/ml), IL-3 (200 U/ml) and GM-CSF (200 U/ml). The highly enriched progenitor cell content of this fraction of cells is demonstrated by the 53±7% cloning efficiency (mean ± 1 SEM; range 32 to 77% for 5 experiments) for total colonies (CFU-GM, BFU-E and CFU-GEMM), stimulated under these conditions when chemokines were not present. As shown in FIG. 2, rmuMIP-1α as well as the hu preparations of MIP-1α, MIP-1β, IL-8, PF4 and MCAF significantly suppressed colony formation of CFU-GM, BFU-E and CFU-GEMM by 30–70%. MIP-1β, MIP-2β, GRO-α, NAP-2 and RANTES were without effect on these purified cells. Since a highly enriched population of progenitor cells was used, and suppression was similar to that seen using relatively unseparated LD cells (FIG. 1), the results evidence that rhuMIP-1α, rhuMIP-2α, rhuIL-8, huPF4 and rhuMCAF are directly suppressing myeloid progenitor cell proliferation.

Figure 3A:
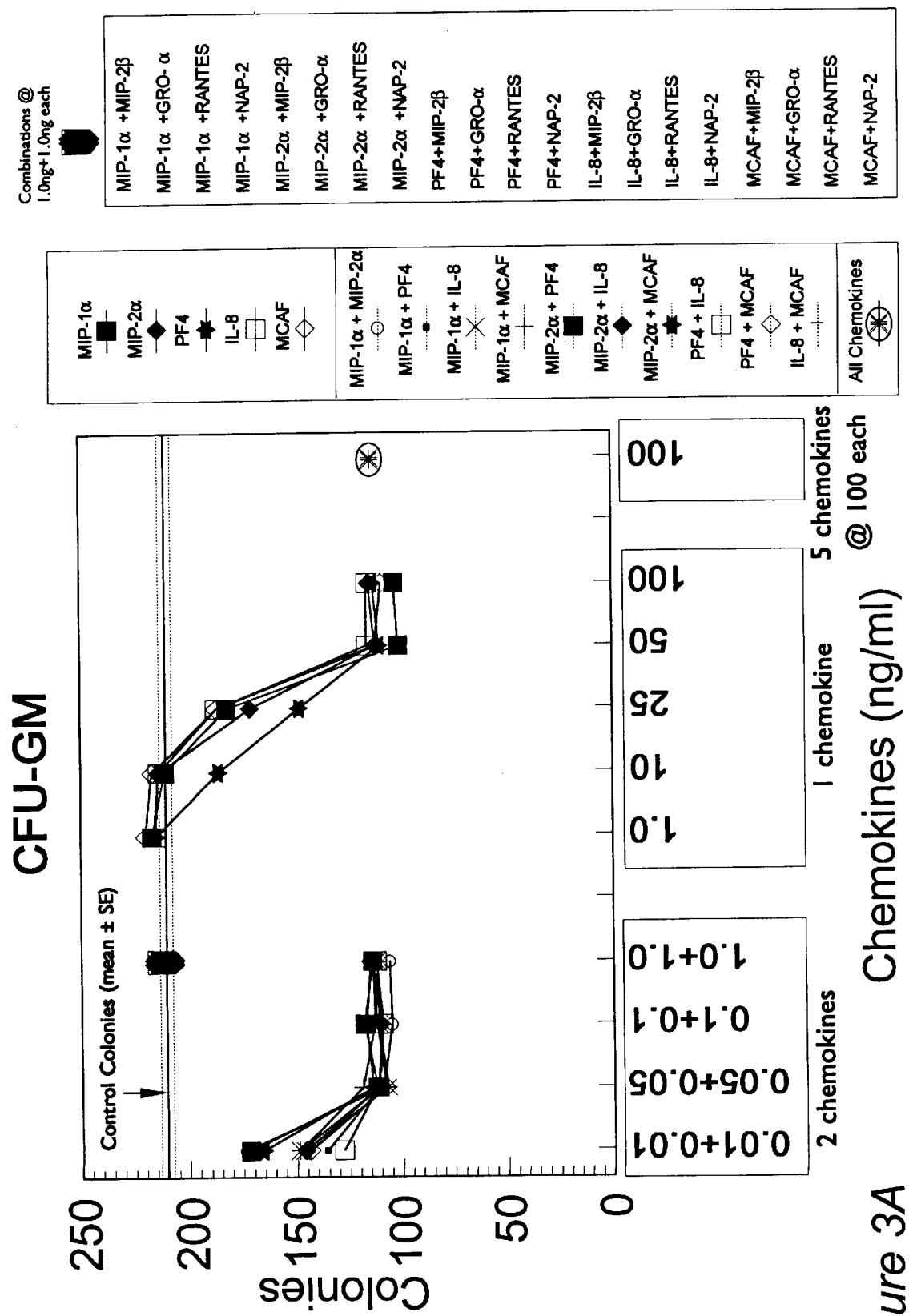
FIG. 3: Influence of chemokines, alone and in combination, on colony formation by: A) CFU-GM, B) BFU-E, and C) CFU-GEMM in low density bone marrow cells stimulated by GM-CSF and SLF for CFU-GM, and by Epo and SLF for BFU-E and CFU-GEMM. The key for symbols is to the right of each of the graphs. The symbols in the graph are each inclusive of the mean plus SEM bars. In some cases points were so close together that they clustered into one pattern, the most striking of which is shown for the combinations of chemokines at 1.0 ng+1.0 ng each in the key to the far right.
Figure 3B:
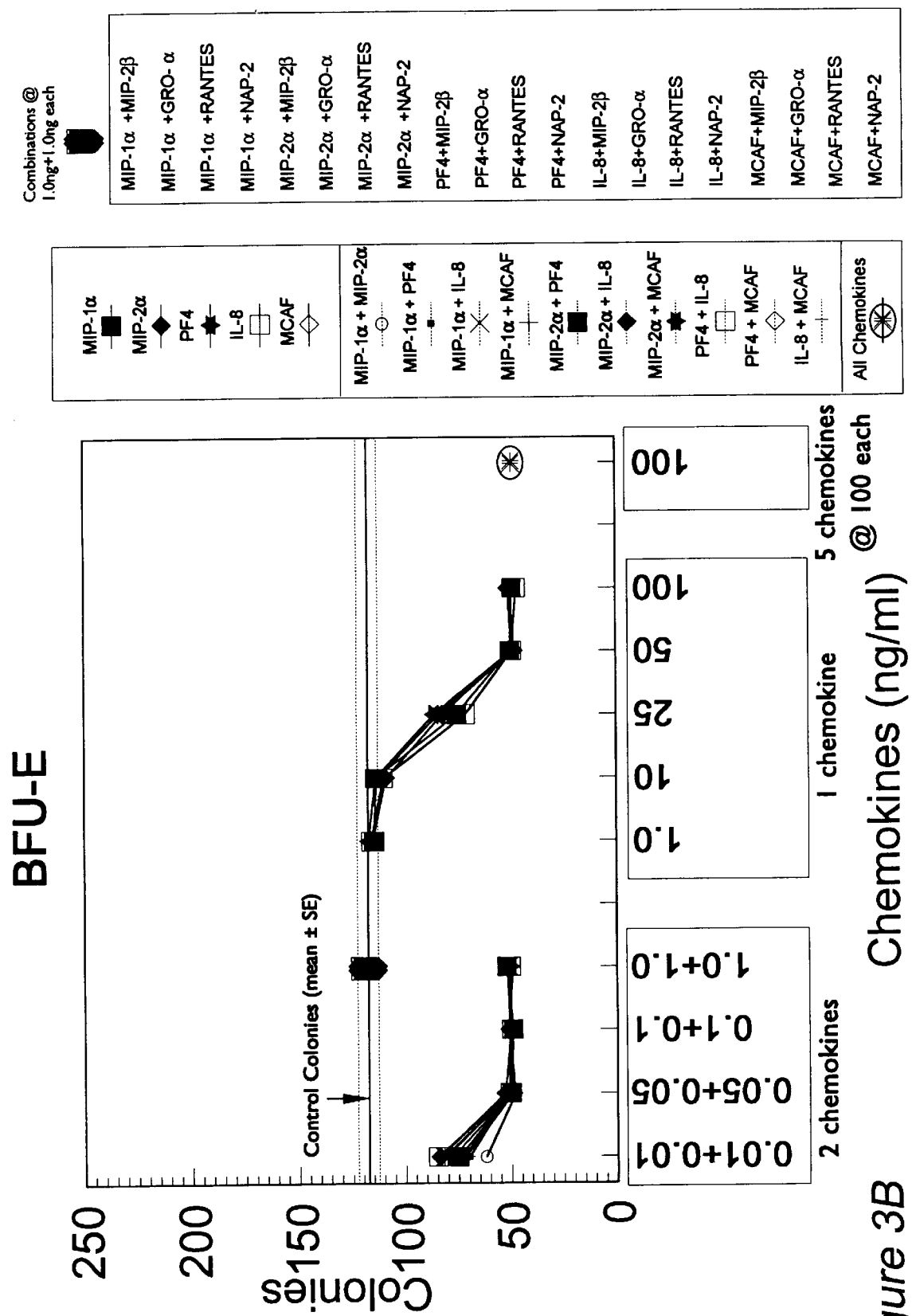
Figure 3C:
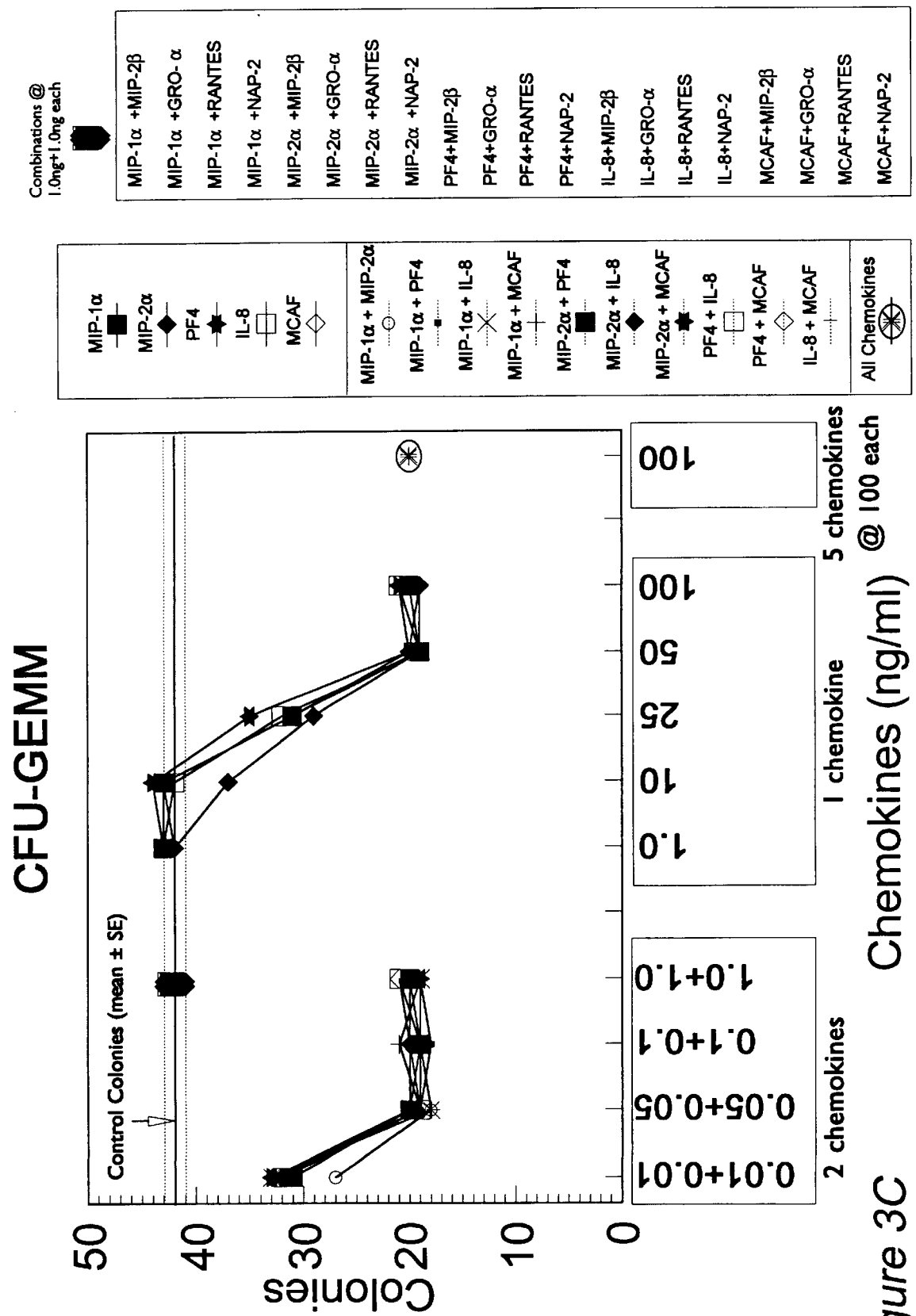

Effects of Combinations of Chemokines at High Concentration: Suppressive Activity In order to determine if greater suppressive activity could be obtained than that noted in FIG. 1, combinations of the chemokines with suppressive activity were first assessed at 100 ng/ml each for effects on colony formation by CFU-GM in LD marrow cells stimulated by rhuGM-CSF (100 U/ml) and rhuSLF (50 ng/ml) (FIG. 3A) and on colony formation by BFU-E (FIG. 3B) and CFU-GEMM (FIG. 3C) in LD marrow cells stimulated by rhuEpo (1 U/ml) and rhuSLF (50 ng/ml). The chemokines were added to the plates prior to adding the cells. As shown, the addition of 100 ng/ml each of MIP-1α, MIP-2α, PF4, IL-8 and MCAF had no greater suppressive effect than that of any one of these chemokines alone. Not shown are data that combinations of two, three or four of these chemokines at 100 ng/ml each also had no greater suppressive effect than that of one of these chemokines.

Effects of Combinations of Chemokines at Low Concentrations: Suppressive Activity The effects on colony formation of low concentrations of combinations of two of each of the five suppressive cytokines (MIP-1α, MIP-2α, PF4, IL-8 and MCAF) were assessed. In a first experiment in which the dose response of each cytokine alone was equal to that noted in Table 1, and no suppressive activity was seen at either 10 or 1 ng/ml of each chemokine, the combination of any two of the five suppressive cytokines at 0.1 ng/ml plus 0.1 ng/ml resulted in significant maximal suppression (p<0.001) of colony formation by CFU-GM, BFU-E and CFU-GEMM. In a second such experiment shown in FIGS. 3A–C, in which the effects of combinations of cytokines were titrated to lower concentrations, it is apparent that the combination of any two of the five suppressive cytokines, on a weight to weight basis, results in significant suppression with up to 2500 fold less protein than when any of these five cytokines is used alone.

An assessment was also made whether such synergistic suppression was possible if a low concentration (1.0 ng/ml) of MIP-1α, MIP-2α, PF4, IL-8, or MCAF was added with 1.0 ng/ml of the following chemokines which at high concentrations (up to 1000 ng/ml) had no suppressive activity on their own: MIP-2β, GRO-α, Rantes and NAP-2. From the results shown in FIGS. 3A–C, it is apparent that the combination of low concentrations of the chemokines that do not have suppressive activity at higher concentrations with concentrations of MIP-1α, MIP-2α, PF4, IL-8 and MCAF that each alone do not have suppressive activity, does not result in suppressive activity. Thus, only the chemokines that have suppressive activity alone can act together at low concentrations to synergistically suppress the growth of myeloid progenitor cells. From the results in Table 2, it is also apparent that low concentrations of each of two of the five suppressive chemokines can synergise to suppress colony formation of CFU-GM, BFU-E and CFU-GEMM in a population of CD34⁺⁺⁺ sorted marrow cells in which±88% of the cells are progenitors. This evidences that the synergistic suppression noted is mediated directly on the progenitors themselves rather than via an action on accessory cells.

Effects of Combinations of Chemokines: Blocking Activity

Figure 4:
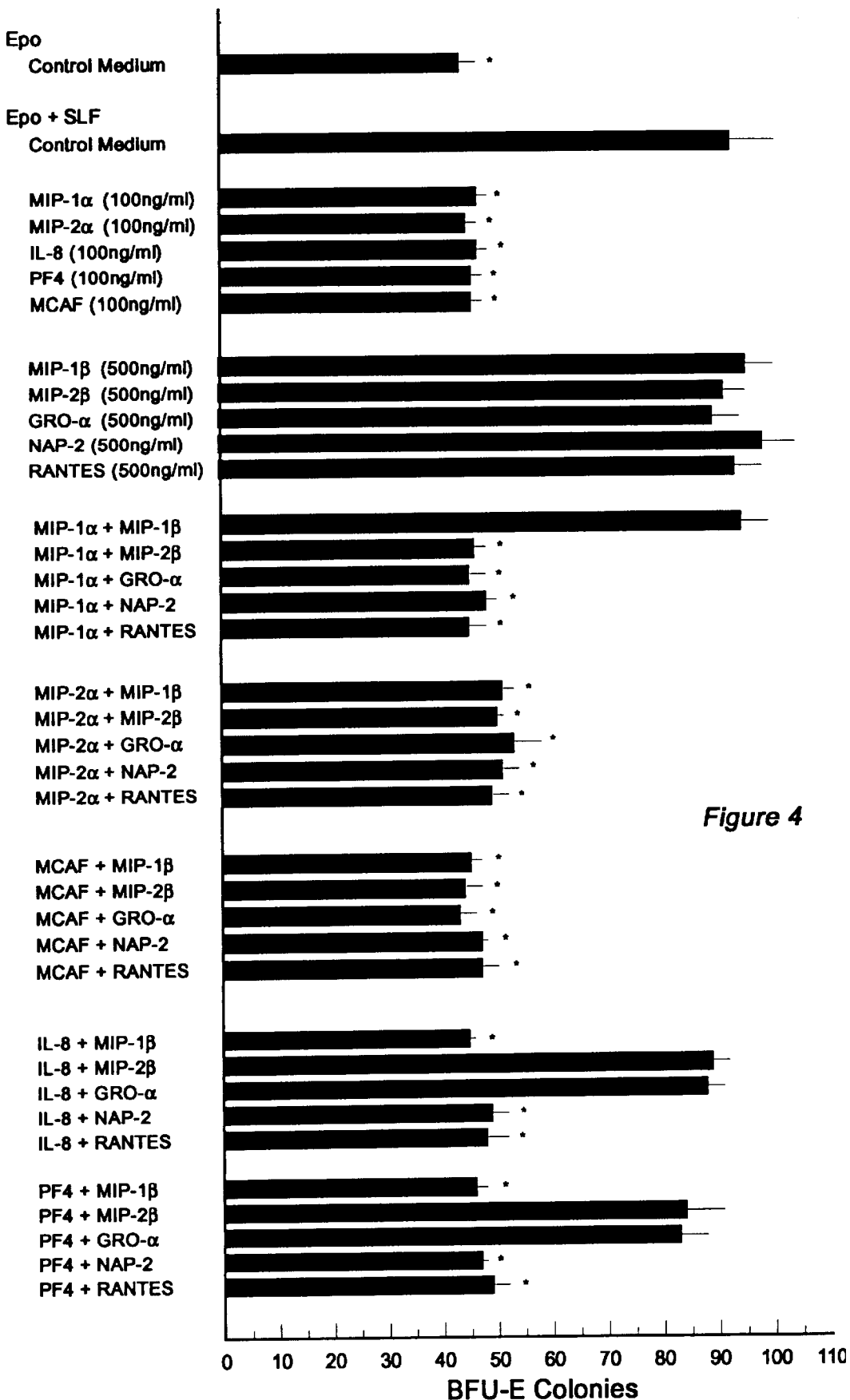
FIG. 4: Influence of combinations of suppressive and non-suppressive chemokines on colony formation by BFU-E present in $10^5$ low density normal human bone marrow cells/ml. Chemokines were added to plates prior to adding cells. "*" designates significant decrease (p<0.001) compared to cells grown in the presence of Epo plus SLF; other values not significantly different from control of Epo plus SLF.

An assessment was made of the effects on colony formation of 5-fold excess amounts of the hu cytokines that did not demonstrate suppressive activities (500 ng/ml of either MIP-1β, MIP-2β, GRO-α, NAP-2 and RANTES) when added with cytokines with suppressive activity (100 ng/ml of either MIP-1α, MIP-2α, PF4, IL-8 and MCAF) (FIG. 4, one of 2 reproducible experiments using BFU-E-colony formation as the test assay). The chemokines were added together in the plates prior to addition of the cells. MIP-1β blocked the suppressive effects of MIP-1α. MIP-2β and GRO-α blocked the suppressive effects of IL-8 and PF4. At least at the ratios of chemokines assessed (5:1), MIP-1β did not block the suppressive effects of MIP-2α, IL-8, PF4 of MCAF; MIP-2β and GRO-α did not block the suppressive effects of MIP-1α, MIP-2α, or MCAF. NAP-2 or RANTES did not block the suppressive effects of MIP-1α, MIP-2α, IL-8, PF4 or MCAF. Similar effects were also noted in two experiments each using colony formation of CFU-GM or CFU-GEMM as a test assay.

Figure 5:
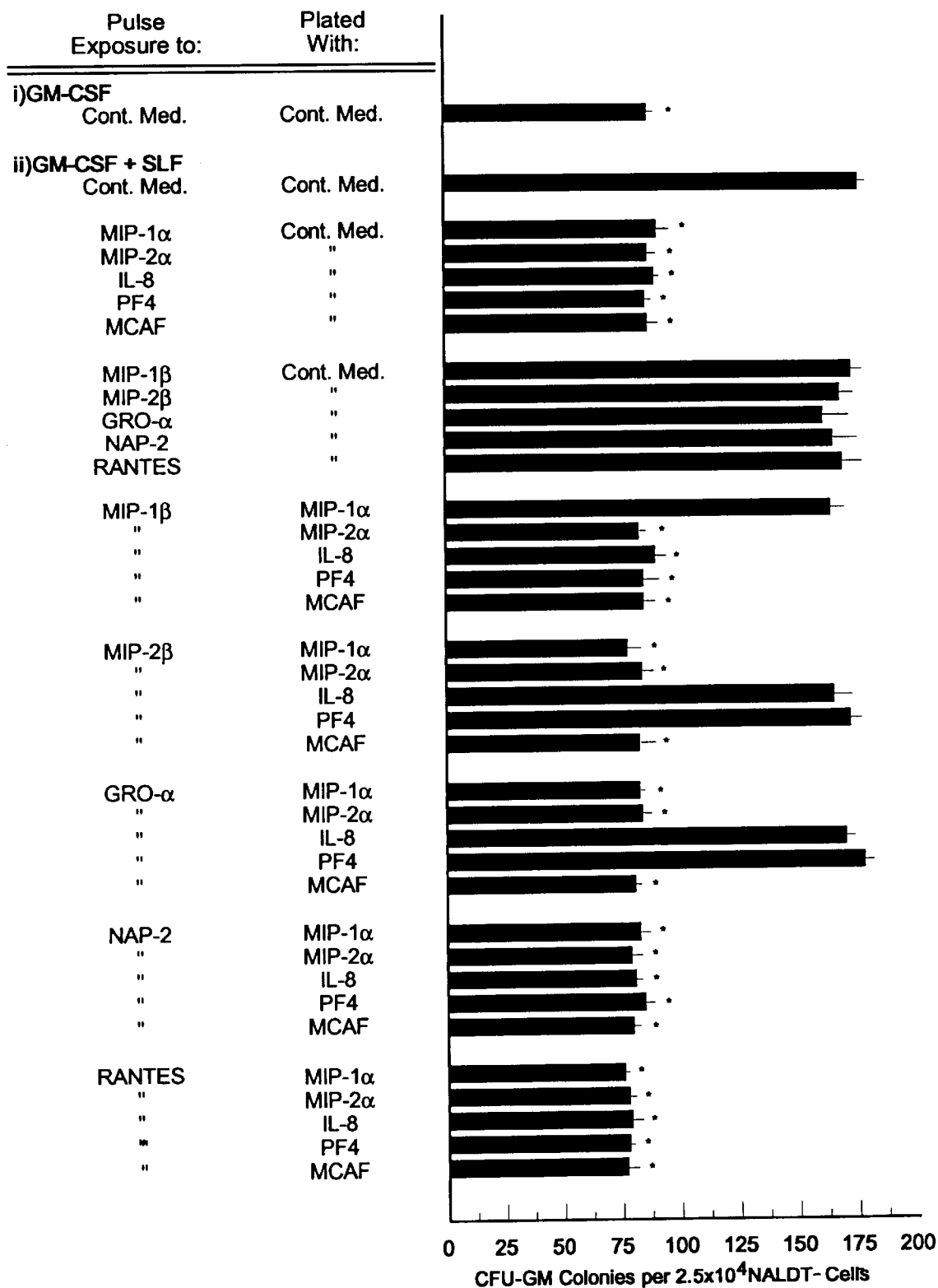
FIG. 5: Influence of pulse exposure of NALDT⁻ normal human bone marrow cells to chemokines on effects of subsequent exposure of these cells to other chemokines. "*" designates significant decrease, p<0.01, compared to cells grown in the presence of GM-CSF plus SLF; other values not significantly different from control of GM-CSF plus SLF.

Also assessed were the effects on colony formation of pulse exposure of NALDT⁻ bone marrow cells to the various hu chemokines in terms of the suppressive and blocking activities of these molecules. As shown in FIG. 5 (one of two reproducible experiments using colony formation of CFU-GM as the test assay system), pulse exposure of cells to MIP-1α, MIP-2α, IL-8, PF4 and MCAF for 1 hour at 4° C. with 100 ng chemokine/10⁵ cells prior to washing cells 2× and plating in the presence of GM-CSF (100 U/ml) and SLF (50 ng/ml) resulted in about 50% inhibition of total colony formation and in complete suppression of the SLF-enhanced colony formation. Not shown in this figure is that after cells had been pulsed with either MIP-1α, MIP-2α, IL-8, PF4 or MCAF, colony numbers were not further changed by the subsequent addition to the plates of 100 ng/ml MIP-1α, MIP-2α, IL-8, PF4 or MCAF or 500 ng/ml of MIP-1β, MIP-2β, GRO-α, NAP-2, or RANTES. Pulse exposure of cells to MIP-1β, MIP-2β, GRO-α, NAP-2, or RANTES, at 500 ng/10⁵ cells, had no significant effect (p>0.05) on cells stimulated with GM-CSF and SLF (FIG. 5). However, pulse exposure of cells to MIP-1β blocked the suppressive effect of subsequently added MIP-1α to the plates, and pulse exposure of cells to MIP-2β or GRO-α each blocked the suppressive effects of subsequently added IL-8 or PF4 to the plates. Similar results were seen in two experiments in which colony formation by BFU-E or CFU-GEMM served as the test assay system. The results of the pulsing experiments (FIG. 5) thus reproduce the effects seen when combinations of chemokines were added directly to the plates without pulsing of the cells (FIG. 4). These effects are consistent with receptor-mediated events.

Effects of Monomeric vs. Polymerized Chemokines: Suppressive Activity

Figure 6A:
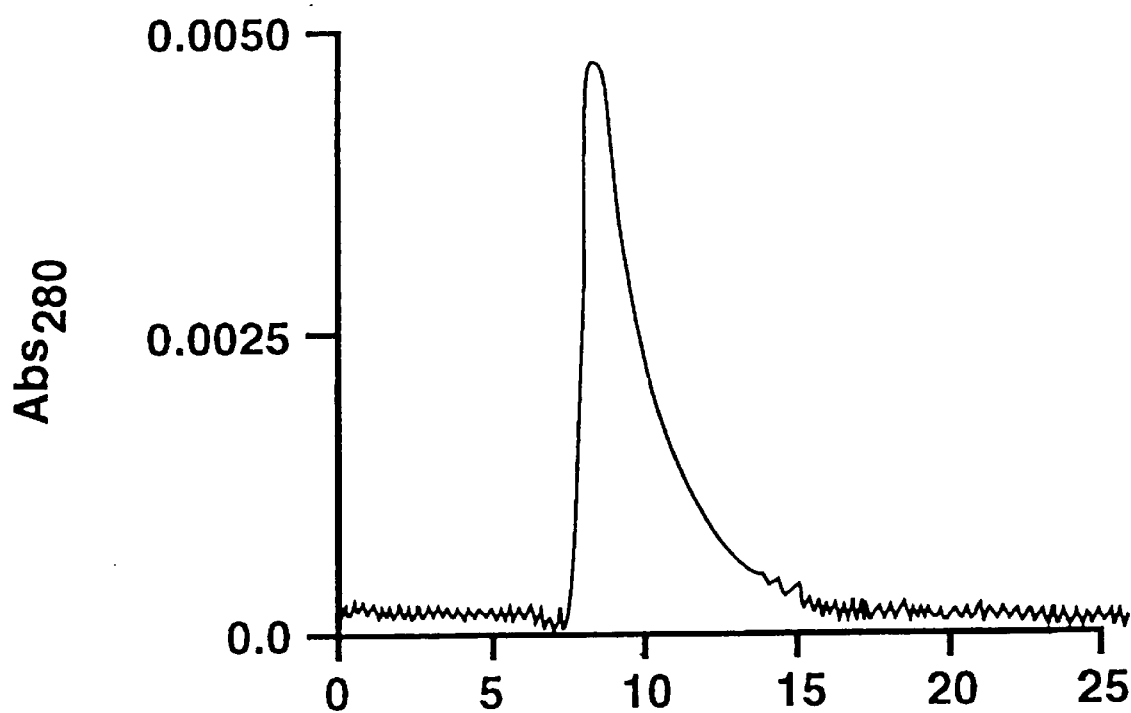
FIG. 6: Gel filtration chromatography and quantitation of MIP-1α. Shown are representative elution profiles of rmuMIP-1α from a stock solution of ACN: A) diluted in PBS to a final concentration of>20 ng/ml and eluted with PBS, and B) both diluted and eluted in ACN. Superose-12 columns (Parmacia, Uppsala) were pre-equilibrated with appropriate buffers, 0.2 ml sample (7 μg MIP-1α) was injected, and columns were eluted at a flow rate of 0.5 ml/min. Protein elution was continuously monitored by absorption at 280 nm wavelength using FPLC system (Pharmacia). Columns were calibrated for molecular weight using a marker kit from Bio Rad (Richmond, Calif.). Calibration was done independently in each buffer. Quantitation of MIP-1α (C) was accomplished by immunoblotting of SDS-PAGE-separation 8 KD samples with anti-MIP-1α antibodies and subsequent densitometry. Lanes 1 to 5 contain respectively 0.1, 0.5, 1.0, 2.0, and 3.0 ng/ml MIP-1α from stock solutions in ACN. Lanes 6 and 7 respectively contain $10^{-3}$ and $10^{-2}$ dilutions of polymerized MIP-1α from the peak in A. Lanes 8 and 9 respectively contain $10^{-1}$ dilution and undiluted monomeric MIP-1α from the portion of A that corresponds to the peak in B. After densitometric scanning, peak areas of lanes 1 to 5 were plotted against rmuMIP-α concentrations to generate standard curves (D) from which concentrations of MIP-1α, such as those in lanes 6 to 9 were extrapolated ($r^2$=0.95). For western blot analysis, MIP-1α samples were boiled for 5 min. in SDS sample buffer containing 2 mercaptoethanol and subjected to 15% SDS-PAGE. Proteins resolved on the gel were transblotted onto Immunobilon-P membrane (Millipore Corp., Bedford Mass.) and visualized by staining.
Figure 6B:
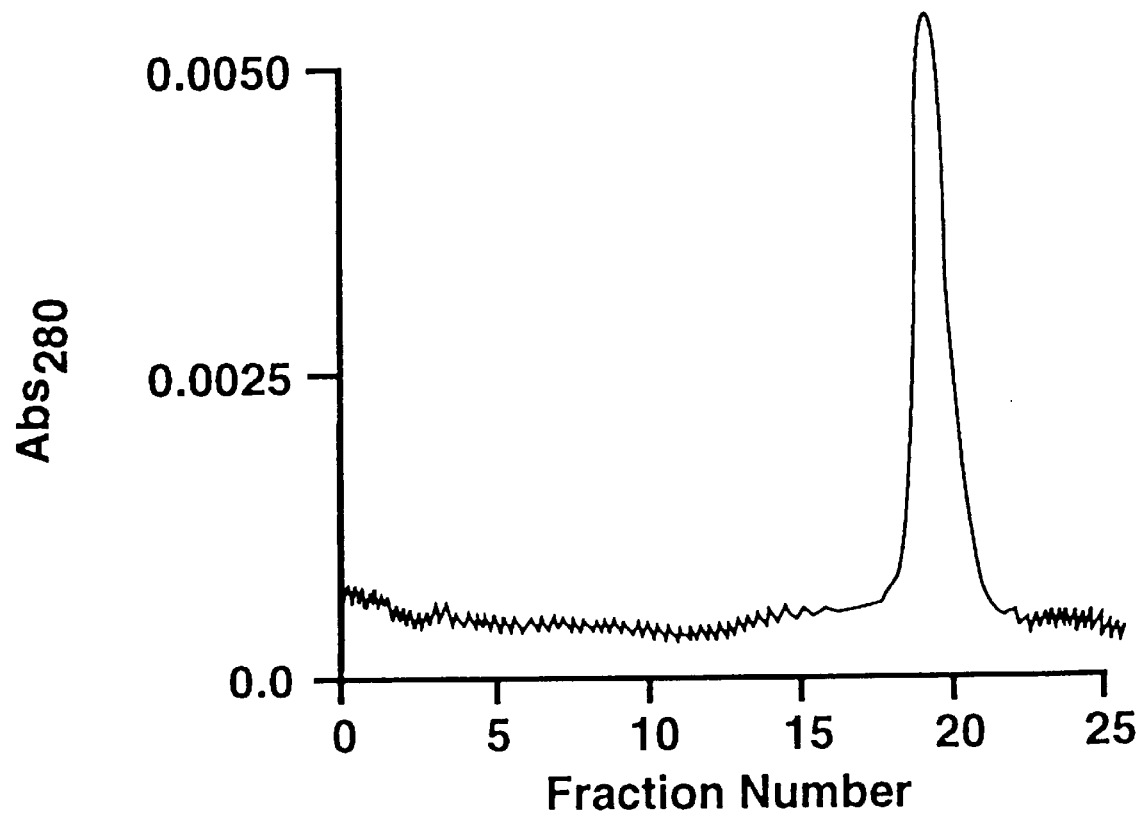
Figure 6C:
Figure 6D:
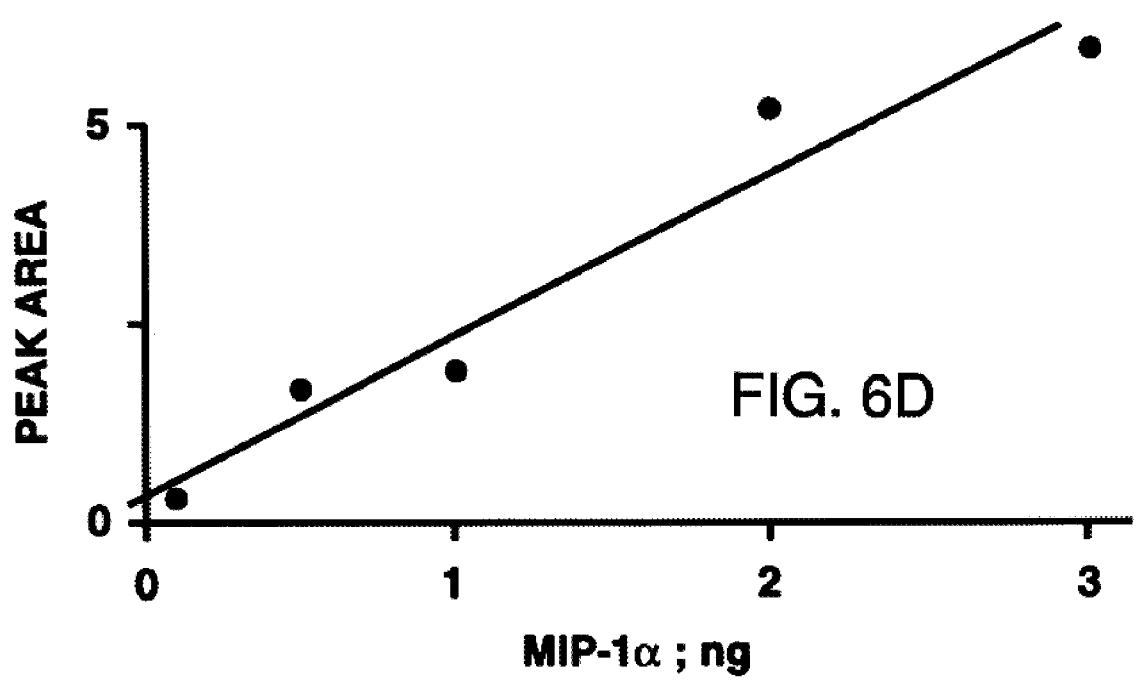

The suppressive effects of monomeric versus polymerized forms of chemokine were assessed. RhuMIP-1α was purchased from R&D Systems (Minneapolis, Minn.) in 30% acetonitrile (ACN) and 0.1% trifluoroacetite acid without protein carriers. After gel filtration chromatography on a Superose-12 column in this buffer, rmuMIP-1α was in monomeric form with an approximate molecular weight of 8 KD (FIG. 6B). However, when MIP-1α, in ACN, was diluted 1:20 with phosphate buffered saline (PBS) to a final concentration of greater than 20 ng/ml and assessed by gel filtration chromatography in PBS,>99.7% of the recovered protein eluted in polymerized form of about 650 KD (FIG. 6A). Treatment with 1M NaCl did not dissociate the molecule. However, treatment with 2% sodium dodecyl sulphate (SDS) at 100° C. for 20 min. in the presence of 5% 2-mercaptoethanol completely dissociated the molecule into 8 KD monomeric form (FIG. 6C). A standard curve for the SDS-dissociated MIP-1α is assessed by immunoblotting with rabbit anti rmuMIP-1α is shown in FIG. 6D. Because of the polymerized nature of MIP-1α in PBS, immunoblotting of SDS-polyacrylamide gel electrophoresis (PAGE)-separated MIP-1α probably allows a more accurate estimate of its actual concentration than obtainable by ELISA or radioimmunoassay assay.

Figure 7:
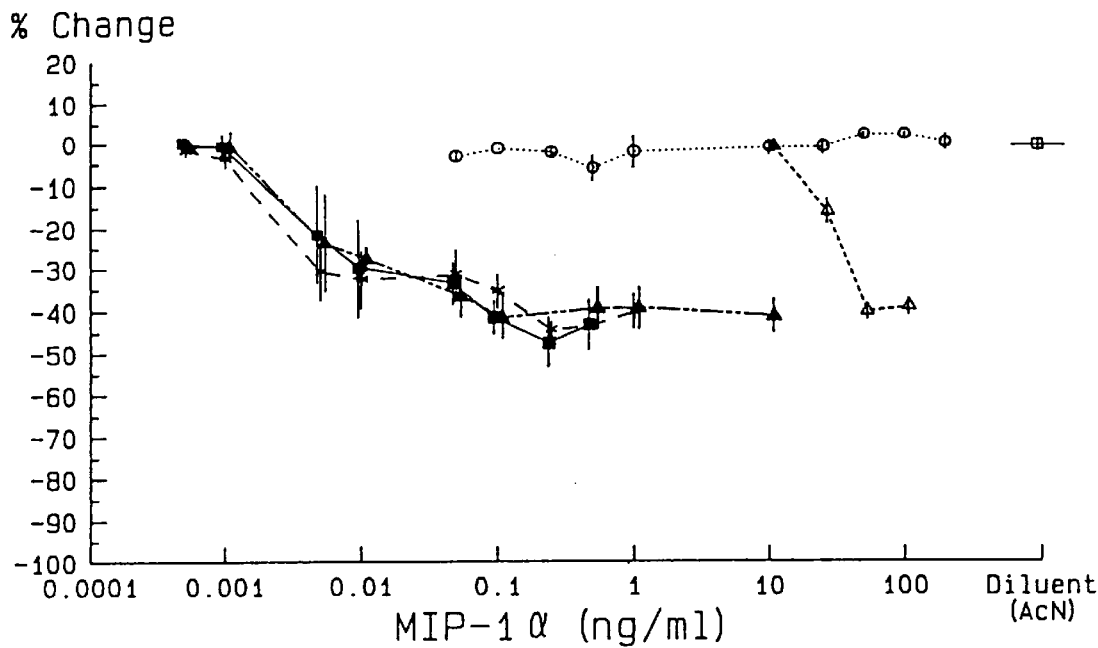
FIG. 7: Influence of purified monomeric and purified polymerized rmuMIP-1α on proliferation of mouse marrow CFU-GM. The axis for MIP-1α concentration is log scale. MIP-1α preparations were assayed for effects on colony formation by $7.5 \times 10^4$ bone marrow cells per ml from $BDF_1$ mice (Jackson Laboratories, Bar Harbot, MEO plated in 0.3% agar-culture medium in the presence of 100 U/ml rmuGM-CSF and 50 ng/ml rmuSLF Immunex Corp. Seattle Wash.). Colonies (>40 cells/group) containing neutrophilic granulocytes and/or monocytes, macrophages were sorted (3 plates/determination) after 6–7 days incubation at 5% $Co_2$ in lowered (5%) $O_2$ tension. Results are expressed as mean percentage change±1 SEM from control (McCoy's) medium for: MIP-1α from a stock solution in ACN diluted in PBS to a final concentration of>20 ng/ml (...Δ...; 7 experiments), monomeric MIP-1α from a stock solution in ACN diluted in PBS to a final concentration of>20 ng/ml which was separated by gel filtration (FIG. 6A) (–*–; 4–8 experiments; including 2 experiments in which monomeric MIP-α from the column was left in PBS collection medium (<5 ng/ml) at 4° C. for up to 3 weeks), polymerized MIP-1α which formed in PBS at a final concentration of>20 ng/ml and was separated by gel filtration (FIG. 6A) (...o...; 3–7 experiments; including 2 experiments in which polymerized MIP-1α from the column was left in PBS collection medium (>350 ng/ml) at 4° C. for up to 3 weeks), MIP-1α from a stock solution in ACN diluted in PBS to a final concentration of ≤5 ng/ml (■); 3–4 experiments), separated MIP-1α polymer placed into ACN solution and incubated overnight prior to dilution in PBS to a final concentration of≤5 ng/ml (Δ; 2–4 experiments), and ACN diluent alone (□: 8 experiments with dilutions of ACN found in MIP-preparations assayed for activity). Control numbers of colonies for the 8 experiments ranged from 67±3 to 137±12.
Figure 9A:
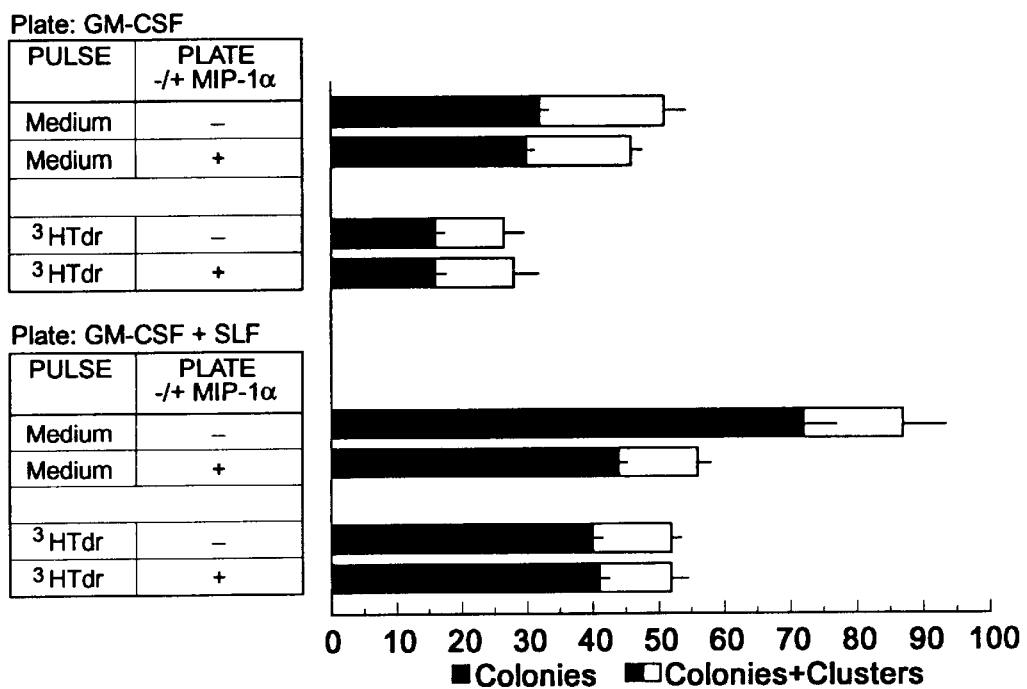
FIG. 9: Influence of CFU-GM cell cycle on responsiveness of cells to inhibition by rmuMIP-1α. In part A, $BDF_1$ mouse marrow cells were pulse-treated with either control (McCoy's) medium or high specific activity tritiated thymidine ($^3$HTdr, 50 uCi/ml, specific activity: 20 Ci/mmol) for 30 min. at 37° C. prior to washing cells 2× and plating cells in the presence of control diluent (ACN) or 0.1 ng/ml monomeric rmuMIP-1α. In part B, marrow cells were pulsed for 30 min. at 37° C. first with either control (McCoy's) medium, diluent (ACN), $^3$HTdr, or MIP-1α and washing cells 2×. Pulsed cells were plated in the presence of diluent of 0.1 ng monomeric rmuMIP-α/plate. Decrease in colony formation after pulse exposure of cells to high specific activity $^3$HTdr estimates of the percent of CFU-GM in DNA synthesis (S)-phase of the cell cycle at the time of pulse exposure. Cells in part A were stimulated by 100 U/ml rmuGM-CSF, or 100 U/ml rmuGM-CSF plus 50 ng/ml rmuSLF. Cells in part B were stimulated by GM-CSF plus SLF. Colonies and clusters (3–40 cells/group) are expressed per $7.5 \times 10^4$ cells/plate. Two experiments are shown and similar results were seen also in one other experiment.

Preparations of rmuMIP-1α were assessed for suppressive activity on colony formation by CFU-GM in $BDF_1$ bone marrow cell cultures stimulated by GM-CSF plus SLF (FIG. 7). MIP-1α diluted in PBS to>20 ng/ml suppressed total colony formation by about 40% at 50 to 100 ng/ml (p<1; two tailed student's t test). Activity was lost at ≦10 ng/ml, and up to 1000 ng/ml was no more suppressive than 100 ng/ml. MIP-1α does not suppress colony formation stimulated by only GM-CSF, and inhibition was actually 100% of the enhanced number of colonies seen with cells stimulated by GM-CSF plus SLF compared to GM-CSF alone (this phenomenon is seen in FIG. 9A).

After separation of the MIP-1α diluted in PBS (FIG. 6A), the monomeric form (too little to be detected by UV absorption) was the only active form. The monomer was suppressive at concentrations to 0.005 ng/ml (p<0.01). Separated MIP-1α polymer, up to 300 ng/ml, was not active (p>0.1). Three weeks after storage at 4° C., the separated monomeric MIP-1α in PBS was still as active as that assayed immediately after collection, and the separated polymerized MIP-1α was still inactive (FIG. 7). Rechromatography demonstrated that the monomer remained monomer and the polymer remained polymer. Since monomer was separated at low concentration, this suggested that the physical stability of both forms of MIP-1α might relate to the concentration of MIP-1α in PBS. When MIP-1α in ACN was diluted into PBS at a final concentration ≦5 ng/ml, the curve for suppression was superimposeible with that of the separated monomeric form of MIP-1α (FIG. 7). Incubation of separated MIP-1α polymer in ACN for about 18 hours at 4° C. resulted in the reappearance of monomeric MIP-1α and active suppressive activity (FIG. 7).

Monomeric and polymerized rmuMIP-α fractions were also assessed for effects on colony formation of normal hu bone marrow cells. Separated MIP-1α polymer had no significant effect on colony formation at 50 to 200 ng/ml (+2 to −5% change from control values of 58±4 CFU-GM colonies/$10^5$ cells stimulated with rhuGM-CSF and rhuSLF; p>0.1). Separated MIP-1α monomer, at the lowest concentration assessed, 0.5 ng/ml, suppressed colony formation by 53% (p<0.001). Monomeric MIP-1α (0.5 ng/ml) also suppressed by 44 to 54% colony formation of by marrow BFU-E and CFU-GEMM (p<0.0001; control colonies: 79±6 BFU-E, 26±3 CFU-GEMM, stimulated by rhuEpo and rhuSLF). Separated MIP-1α polymer, at 50 to 200 ng/ml, had no effect on colony formation by BFU-E or CFU-GEMM. Monomeric MIP-1α was without effect on hu colony formation by CFU-GEMM stimulated with only rhuGM-CSF and by BFU-E an CFU-GEMM stimulated with only rhuEpo.

Figure 8:
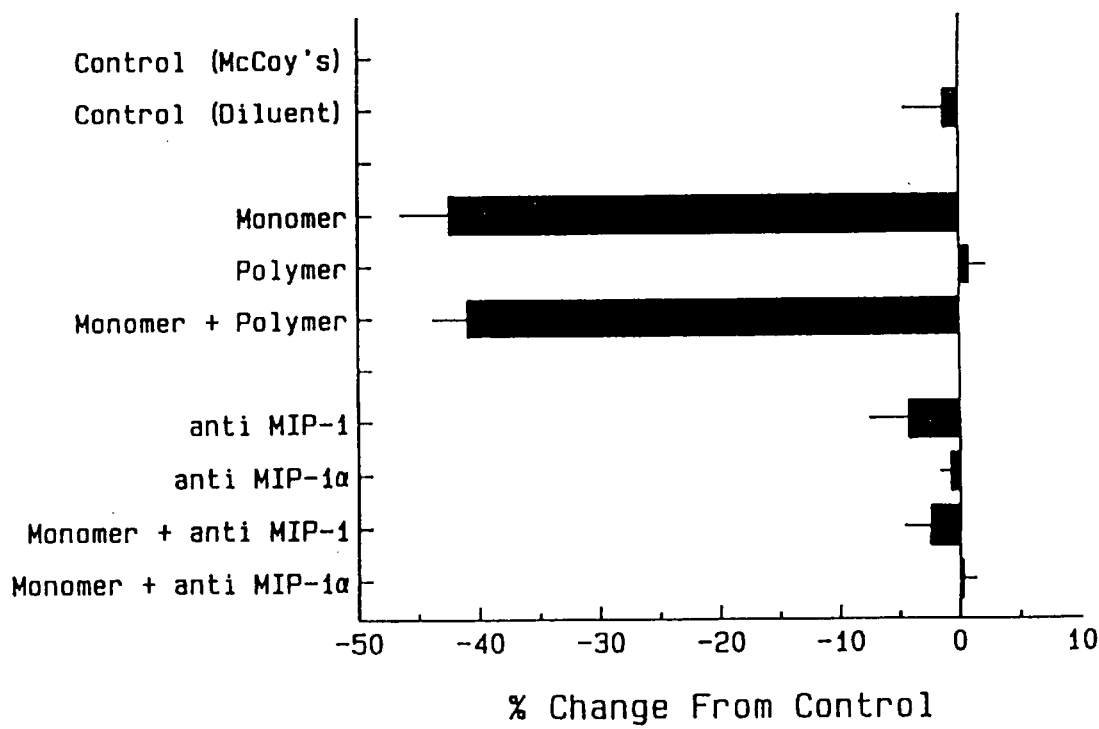
FIG. 8: Influence of separated rmuMIP-1α polymer and anti-MIP-1α on myelosuppression by monomeric rmuMIP-1α on mouse marrow CFU-GM. Results of 4 experiments are expressed as mean percentage change±1 SEM of colony formation compared to control (McCoy's) medium. Assays were performed as in FIG. 2 and percentage changes are based on control colony numbers of 83±4, 137±12, 121±4 and 91±5. Monomeric and polymerized rmuMIP-1α were obtained after column separation as in part A of FIG. 1 and were assayed, at monomer to polymer concentrations (ng/ml) of 0.1:50.0, 0.4 to 300.0, 2.4 to 81.0 and 0.005:12.5 (respective monomer:polymer ratios of 1:500, 1:750, 1:34 and 1:2500). For antibody neutralization studies, amounts of monomeric rmuMIP-1α which yielded final concentrations of 0.4 to 2.4 ng/ml MIP-1α in the test plates were preincubated with either control (McCoy's) medium or the purified immunoglobin fractions of polyclonal rabbit anti-natural muMIP-1or rabbit anti-rmuMIP-α for 1 hour at room temperature.

As seen in FIG. 8, the separated polymerized form of rmuMIP-1α, even at a polymer to monomer ratio of 2500 to 1, did not block the suppressive activity of the monomer. Moreover, the suppressive activity of the monomeric MIP-1α was completely neutralized by preincubation of monomeric MIP-1α with both the polyclonal antibodies against the natural muMIP-1, which recognizes MIP-1α, and against the rmuMIP-1α (FIG. 8). This substantiates the identity of MIP-1α as the sole suppressive agent in the preparation.

Figure 9B:
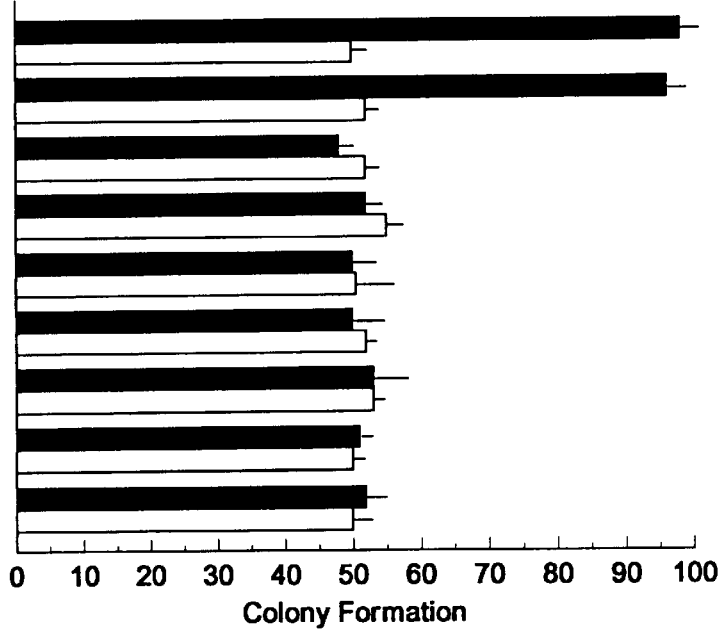

To evaluate whether monomeric MIP-1α acted on the DNA synthesis (S)-phase of the cell cycle, monomeric MIP-α was assessed for effects on colony formation of mouse marrow cells in which the cells were first pulse-treated with high specific activity tritiated thymidine ($^3$HTdr) to remove cells in S-phase of the cell cycle prior to addition of MIP-α to the cultures (FIG. 9A). While CFU-GM that formed colonies in the presence of GM-CSF, or GM-CSF plus SLF, each had about 40–50% of cells in cycle at the start of the culture, only the CFU-GM stimulated by GM-CSF plus SLF were suppressed by MIP-1α. Addition of MIP-la to cells stimulated with GM-CSF plus SLF that had survived pretreatment with $^3$HTdr, namely cells not in S-phase, did not influence colony formation. These results evidenced that MIP-1α initiates its suppressive effects during S-phase of the cell cycle. Even though the specific activity of the MIP-α used here is about 1000 fold increased compared to that reported previously, (see, Graham et al., *Nature*, Vol. 344, pp. 442 (1990); Broxmeyer et al., *Blood*, Vol. 76, pp. 1110 (1990); Broxmeyer et al., *J. Immunol.*, Vol. 147, pp. 2586 (1991); and Bodine et al., *Blood*, Vol. 78, pp. 914 (1991), suppression is still restricted to the relatively immature populations of progenitors. S-phase specificity was more rigorously substantiated by results in FIG. 9B (cells were stimulated with GM-CSF plus SLF). Suppression was the same whether cells were plated in MIP-1α or pulsed with $^3$Tdr or MIP-1α, pulsed with $^3$HTdr followed by pulsing with MIP-1α or pulsed with MIP-1α followed by pulsing with $^3$HTdr. Addition of MIP-1α to cells pulsed with these combinations did not further decrease colony numbers.

These results demonstrate that monomeric forms of chemokines such as MIP-1α, MIP-2α, PF4, IL-8 and MCAF are suppressive and can be used in amounts far lower than their corresponding forms substantially comprised of their polymers. Furthermore, the in vivo methodology in mice of Maze at al., J. Immunol 149: 1004 (1992), was used with monomeric MIP-1α to determine that this is also true in vivo. Thus, when mice (C3H/HeJ mice, Jackson Laboratories, Bar Harbor, Me.) were used in vivo testing as described in R. Maze et al., supra, except using a substantially monomeric MIP-1α preparation, myelosuppressive effects in vivo were also demonstrated, and this suppression with monomeric chemokine was seen in vivo with 2500-fold less, on a weight-weight basis, than the MIP-1α material used in previous reports (see, Maze, et al., supra, Dunlop, et al., supra, and Lord, et al., supra.

All publications cited herein are hereby incorporated by reference in their entirety as if fully set forth.

While the invention has been illustrated and described in detail in the foregoing description, the same is to be considered as illustrative and not restrictive in character, it being understood that only the preferred embodiment has been described and that all changes and modifications that come within the spirit of the invention are desired to be protected.

TABLE 1

Dose-Dependent Effects of Suppressive Chemokines on Colony Formation by CFU-GM, BFU-E and CFU-GEMM[a]

| Chemokine | Concentration (ng/ml) | % Inhibition of Colony Formation by: | | |
|---|---|---|---|---|
| | | CFU-GM | BFU-E | CFU-GEMM |
| MIP-1α | 100 | 51 ± 2* | 53 ± 2* | 52 ± 3* |
| MIP-1α | 50 | 51 ± 3* | 54 ± 2* | 58 ± 2* |
| MIP-1α | 25 | 23 ± 3** | 27 ± 4** | 30 ± 3** |
| MIP-1α | 10 | 3 ± 2 | 3 ± 3 | 3 ± 2 |
| MIP-1α | 1 | 2 ± 2 | 2 ± 2 | −1 ± 4 |
| MIP-2α | 100 | 50 ± 4* | 50 ± 4* | 55 ± 5* |
| MIP-2α | 50 | 52 ± 4* | 51 ± 5* | 53 ± 3* |
| MIP-2α | 25 | 24 ± 3** | 19 ± 6** | 23 ± 5** |
| MIP-2α | 10 | 3 ± 3 | 4 ± 4 | 6 ± 3 |
| MIP-2α | 1 | 2 ± 2 | 4 ± 2 | −1 ± 6 |
| PF4 | 100 | 52 ± 3* | 50 ± 4* | 53 ± 4* |
| PF4 | 50 | 52 ± 2* | 50 ± 4* | 57 ± 4* |
| PF4 | 25 | 32 ± 5** | 31 ± 2* | 35 ± 9** |
| PF4 | 10 | 10 ± 1 | 10 ± 9 | 13 ± 7 |
| PF4 | 1 | 2 ± 3 | 5 ± 2 | 7 ± 4 |
| IL-8 | 100 | 52 ± 4* | 52 ± 3* | 55 ± 4* |
| IL-8 | 50 | 46 ± 4* | 50 ± 7* | 52 ± 5* |
| IL-8 | 25 | 26 ± 7** | 39 ± 6** | 33 ± 8** |
| IL-8 | 10 | 6 ± 6 | 8 ± 6 | 4 ± 4 |
| IL-8 | 1 | −1 ± 2 | 3 ± 3 | 2 ± 2 |
| MCAF | 100 | 51 ± 1* | 49 ± 4* | 55 ± 5* |
| MCAF | 50 | 47 ± 3* | 50 ± 4* | 53 ± 3* |
| MCAF | 25 | 25 ± 6** | 22 ± 3** | 28 ± 2** |
| MCAF | 10 | 8 ± 4 | 4 ± 2 | 11 ± 6 |
| MCAF | 1 | 0 ± 4 | 1 ± 2 | 0 ± 2 |

[a]The results shown are the average of assays on four separate marrows. Control colony numbers for CFU-GM plated in the presence of GM-CSF plus SLF, and for BFU-E and CFU-GEMM plated in the presence of Epo plus SLF were respectively 121 ± 2, 212 ± 3, 143 ± 2 and 197 ± 3 for CFU-GM, 122 ± 5, 118 ± 6, 115 ± 4, and 56 ± 5 for BFU-E, and 36 ± 2, 42 ± 1, 33 ± 2 and 58 ± 4 for CFU-GEMM per $10^5$ low density marrow cells/ml/plate.
*designates significant decrease, p < 0.001 compared to control values;
**designates significant decrease p < 0.01 compared to control values; other values were not significantly different from control, p > 0.05.

TABLE 2

Influence of Chemokines, Alone and in Combination, on Colony Formation by Myeloid Progenitor Cells in Sorted CD34[+++] Human Bone Marrow Cells.*

| Chemokine(s) (concentration; ng/ml) | CFU-GM | BFU-E | CFU-GEMM |
|---|---|---|---|
| Control Medium | 176 ± 3 | 30 ± 1 | 15.3 ± 1.8 |
| MIP-1α (50) | 56 ± 5[a] | 5 ± 2[a] | 0.7 ± 0.7[a] |
| MIP-1α (25) | 65 ± 9[a] | 15 ± 2[a] | 2.7 ± 0.7[a] |
| MIP-1α (10) | 85 ± 2[a] | 15 ± 2[b] | 6.7 ± 0.7[c] |
| MIP-1α (1) | 153 ± 10 | 23 ± 3 | 12.0 ± 1.2 |
| MIP-2α (50) | 97 ± 7[a] | 12 ± 1[a] | 4.7 ± 1.3[c] |
| MIP-2α (25) | 112 ± 8[a] | 15 ± 1[a] | 7.3 ± 1.3[d] |
| MIP-2α (10) | 140 ± 7[c] | 18 ± 1[b] | 9.0 ± 1.7 |
| MIP-2α (1) | 170 ± 5 | 27 ± 2 | 13.3 ± 0.7 |
| PF4 (50) | 110 ± 1[a] | 14 ± 2[a] | 6.7 ± 1.3[d] |
| PF4 (25) | 125 ± 7[b] | 18 ± 1[a] | 8.7 ± 1.3[e] |
| PF4 (10) | 147 ± 2[c] | 22 ± 3[d] | 10.7 ± 1.3 |
| PF4 (1) | 167 ± 6 | 26 ± 1 | 12.7 ± 1.8 |
| IL-8 (50) | 98 ± 6[a] | 14 ± 1[a] | 5.3 ± 0.7[c] |
| IL-8 (25) | 116 ± 1[a] | 17 ± 2[a] | 8.0 ± 1.2[d] |
| IL-8 (10) | 139 ± 3[a] | 21 ± 2[c] | 10.7 ± 2.9 |
| IL-8 (1) | 156 ± 13 | 27 ± 3 | 12.0 ± 2.3 |
| MCAF (50) | 58 ± 5[a] | 10 ± 2[a] | 0[a] |
| MCAF (25) | 67 ± 3[a] | 19 ± 3[a] | 0.7 ± 0.7[a] |
| MGAF (10) | 82 ± 5[a] | 18 ± 1[a] | 5.3 ± 1.8[d] |
| MCAF (1) | 127 ± 7[c] | 23 ± 2 | 8.7 ± 1.3 |
| MIP-1α (1) + MIP-2α (1) | 34 ± 2[a] | 5 ± 1[a] | 0[a] |
| MIP-1α (0.1) + MIP-2α (0.1) | 63 ± 7[a] | 9 ± 1[a] | 4.7 ± 0.7[b] |
| MIP-1α (1) + PF4 (1) | 37 ± 1[a] | 9 ± 2[a] | 0.7 ± 0.7[a] |
| MIP-1α (0.1) + PF4 (0.1) | 59 ± 5[a] | 10 ± 3[a] | 1.7 ± 1.7[a] |
| MIP-1α (1) + IL-8 (1) | 27 ± 6[a] | 5 ± 1[a] | 0.7 ± 0.7[a] |
| MIP-1α (0.1) + IL-8 (0.1) | 47 ± 3[a] | 13 ± 2[a] | 2.0 ± 1.1[a] |
| MIP-1α (1) + MCAF (1) | 31 ± 4[a] | 13 ± 3[a] | 2.0 ± 1.2[a] |
| MIP-1α (0.1) + MCAF (0.1) | 85 ± 2[a] | 17 ± 2[a] | 6.7 ± 0.7[c] |
| MIP-2α (1) + PF4 (1) | 26 ± 3[a] | 11 ± 2[a] | 0[a] |
| MIP-2α (0.1) + PF4 (0.1) | 34 ± 3[a] | 19 ± 4[e] | 3.3 ± 1.3[c] |
| MIP-2α (1) + IL-8 (1) | 56 ± 4[a] | 22 ± 2[d] | 8.7 ± 2.4 |
| MIP-2α (0.1) + IL-8 (0.1) | 97 ± 5[a] | 25 ± 2 | 10.7 ± 2.9 |
| MIP-2α (1) + MCAF (1) | 48 ± 5[a] | 13 ± 2[a] | 6.7 ± 1.8[d] |
| MIP-2α (0.1) + MCAF (0.1) | 90 ± 2[b] | 21 ± 1[b] | 8.7 ± 1.3[e] |
| PF4 (1) + IL-8 (1) | 45 ± 3[a] | 15 ± 1[a] | 0[a] |
| PF4 (0.1) + IL-8 (0.1) | 67 ± 5[a] | 17 ± 1[a] | 7.3 ± 0.7[c] |
| PF4 (1) + MCAF (1) | 35 ± 3[a] | 15 ± 3[a] | 3.3 ± 0.7[b] |
| PF4 (0.1) + MCAF (0.1) | 58 ± 6[a] | 20 ± 1[b] | 9.3 ± 0.7[d] |
| IL-8 (1) + MCAF (1) | 39 ± 4[a] | 13 ± 2[a] | 2.7 ± 0.7[b] |
| IL-8 (0.1) + MCAF (0.1) | 76 ± 5[a] | 22 ± 2[c] | 6.7 ± 0.7[c] |

*250 NALDT[−] CD34[+++] human bone marrow cells plated in the presence of Epo (1 U/ml), SLF (50 ng/ml) and rhuIL-3 (200 U/ml), and in the absence and presence of chemokines were scored for CFU-GM colonies (≧40 cells/group) plus clusters (<40 cells/group), and BFU-E and CFU-GEMM colonies after 14 days of incubation. The cloning efficiency for growth in the absence of chemokines for this experiment in which all colonies were scored from the same plates was 88.4% (176 ± 3 CFU-GM plus 30 ± 1 BFU-E plus 15.3 ± 1.8 CFU-GEMM for 250 cells plated).
[a]Significant difference from control medium, p < 0.001; [b]p < 0.005; [c]p < 0.01; [d]p < 0.03; [e]p < 0.05.

What is claimed is:

1. A composition capable of suppressing proliferation of mammalian myeloid cells, comprising:
   a buffered solution of one or more chemokines from the MIP-1α or MIP-1β family which is active to suppress proliferation of mammalian myeloid cells, wherein said one or more chemokines are present at a concentration sufficient to maintain said one or more chemokines essentially in monomeric form.

2. The composition of claim 1 wherein the chemokine is present in said solution at a concentration of about 10 ng/ml or less.

3. The composition of claim 2 wherein the chemokine is at a concentration of 0.005 ng/ml to 10 ng/ml.

4. The composition of claim 1 wherein the solution comprises MIP-1 α.

5. The composition of claim 1 wherein the solution comprises MIP-2 α.

6. The composition of claim 1 wherein the solution comprises PF4.

7. The composition of claim 1 wherein tile solution comprises IL8.

8. The composition of claim 1 wherein the solution comprises MCAF.

9. The composition of claim 1 wherein the solution comprises a combination of chemokines which suppress proliferation of mammalian myeloid cells, said combination exhibiting synergism in the suppression of proliferation of mammalian myeloid cells.

10. A composition comprising:
   a combination of two or more chemokines which suppress proliferation of mammalian myeloid cells, said combination exhibiting synergism in the suppression of proliferation of mammalian myeloid cells, and wherein said combination comprises at least two chemokines selected from the group consisting of MIP-1α, MIP-2α, PF4, IL-8 and MCAF.

11. The composition of claim 10 wherein said synergistic combination of chemokines includes MIP-1 α.

12. The composition of claim 10 wherein the synergistic combination of chemokines includes MIP-2 α.

13. The composition of claim 10 wherein the synergistic combination of chemokines includes PF4.

14. The composition of claim 10 wherein the synergistic combination of chemokines includes IL8.

15. The composition of claim 10 wherein the synergistic combination of chemokies includes MCAF.

16. A composition comprising:
a buffered solution containing a monomeric chemokine selected from chemokines belonging to the MIP-1α and MIP-1β families which is active to suppress proliferation of mammalian myeloid cells, said composition being substantially free from aggregates of said chemokine and further being stable against aggregation of said chemokine for three weeks when stored at a temperature of 4° C., and wherein said chemokine is present at a concentration sufficient to maintain said chemokine essentially in monomeric form.

17. The composition of claim 16 wherein the chemokine is present in said solution at a concentration of about 10 ng/ml or less.

18. The composition of claim 16 wherein said chemokine is MIP-1α.

19. The composition of claim 16 wherein said chemokine is MIP-2α.

20. The composition of claim 16 wherein said chemokine is PF4.

21. The composition of claim 16 wherein said chemokine is IL8.

22. The composition of claim 16 wherein said chemokine is MCAF.

* * * * *